United States Patent [19]

Cox et al.

[11] Patent Number: 4,900,751
[45] Date of Patent: Feb. 13, 1990

[54] 2-PYRIDINYL-PHENYL-SULPHINYL-AND-PHENYL-THIO-BENZIMIDAZOLES HAVING ANTIFLAMMATORY OR GASTIC ACID SECRETION INHIBITION ACTIVITY

[75] Inventors: David Cox; Hossein A. Dowlatshahi, both of Loughborough; David E. Hall, Wymeswold; Anthony H. Ingall; John L. Suschitzky, both of Loughborough, all of England

[73] Assignee: Fisons plc, Ipswich, England

[21] Appl. No.: 100,584

[22] Filed: Sep. 24, 1987

Related U.S. Application Data

[63] Continuation-in-part of Ser. No. 918,832, Oct. 14, 1986, Pat. No. 4,851,419.

[30] Foreign Application Priority Data

| Sep. 27, 1986 | [GB] | United Kingdom | 8623299 |
| Sep. 27, 1986 | [GB] | United Kingdom | 8623301 |
| Mar. 4, 1987 | [GB] | United Kingdom | 8705017 |
| Aug. 20, 1987 | [GB] | United Kingdom | 8719644 |

[51] Int. Cl.⁴ .................. C07D 401/02; A61K 31/44
[52] U.S. Cl. .................................... 514/338; 546/271
[58] Field of Search ....................... 546/271; 514/338

[56] References Cited

FOREIGN PATENT DOCUMENTS 2161160  1/1986  United Kingdom.
0171372  12/1986  European Pat. Off..

*Primary Examiner*—Jane T. Fan
*Attorney, Agent, or Firm*—Marshall, O'Toole, Gerstein, Murray & Bicknell

[57] ABSTRACT

Compounds of formula I,

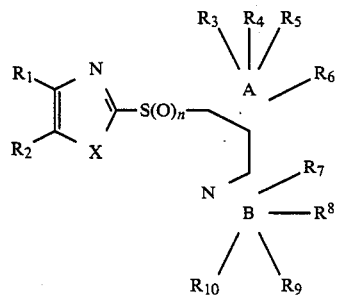

in which A is a 5 or 6 membered, fully unsaturated, carbocyclic or heterocyclic ring, B is a 5 or 6 membered, fully unsaturated, nitrogen containing heterocyclic ring, X is $NR_{19}$, O or S, $R_{19}$ is hydrogen or alkyl optionally substituted by —OCOR, n is 0 or 1, $R_3$, $R_4$, $R_5$, $R_6$, $R_7$, $R_8$, $R_9$ and $R_{10}$ have various significances, $R_1$ and $R_2$, are hydrogen or alkyl or together with the ring carbon atoms to which they are attached, form a benzene or pyridine ring, which ring carries substituents $R_{15}$, $R_{16}$, $R_{17}$ and $R_{18}$, $R_{15}$, $R_{16}$, $R_{17}$ and $R_{18}$, have various significances, with certain provisos are described.

Processes for making the compounds and pharmaceutical formulations containing them, e.g. for the treatment of conditions including excess gastric acid secretion, are also described.

9 Claims, No Drawings

2-PYRIDINYL-PHENYL-SULPHINYL-AND-PHENYL-THIO-BENZIMIDAZOLES HAVING ANTIFLAMMATORY OR GASTIC ACID SECRETION INHIBITION ACTIVITY

This application is a continuation in part of U.S. patent application Ser. No. 918,832, filed Oct. 14, 1986.

This invention relates to new compounds, methods for their preparation and pharmaceutical formulations containing them.

A number of 2-(pyridylmethylsulphinyl) benzimidazoles are known for use as pharmaceuticals from European patent applications Nos. 5129 and 80602 and from British patent application No. 2,134,523. A number of 2-(heterocyclicmethylsulphinyl)benzimidazoles are known from West German OLS 2,548,340 and French Pat. No. 2,392,021.

We have now found a novel group of benzimidazoles, benzoxazoles and benzothiazoles which have pharmacological activity.

According to the invention we provide compounds of formula I,

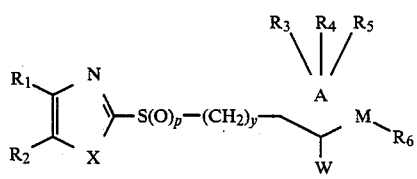

in which A represents a 6 membered fully unsaturated carbocyclic ring, or a 5 or 6 membered nitrogen or sulphur containing saturated, partially unsaturated or fully unsaturated heterocyclic ring, M is a carbon atom, y is 0 or 1, p is 0 or 1

W is $-NR_7R_8$, $-LNR_7R_8$ or is a 5 or 6 membered saturated or fully unsaturated heterocyclic ring containing a nitrogen atom positioned ortho or meta to the point of attachment to ring A, and which ring carries substituents selected from the values of $R_3$ to $R_6$, L is a group containing 1 or 2 carbon atoms, optionally linked to the nitrogen atom by a double bond, in which case $R_7$ has no significance, $R_7$ and $R_8$, which may be the same or different, are each hydrogen, alkyl, phenyl or cycloalkyl, each of which is optionally substituted by phenyl, the phenyl groups in turn optionally being substituted by alkyl, or $R_7$ is as defined above and $R_8$ is $-OR_{13}$ or $-NR_{14}R_{15}$, wherein $R_{13}$, $R_{14}$ and $R_{15}$, which may be the same or different, are each hydrogen, cycloalkyl, alkanoyl, pyridyl, phenyl or alkyl optionally substituted by halogen or by an oxo group, or $R_7$ and $R_8$, together with the nitrogen atom to which they are attached, form a 4 to 8 inclusive membered ring which optionally contains 0, 1 or 2 further hetero atoms, which ring carries substituents selected from the values of $R_3$ to $R_6$, or when W is $NR_7R_8$ and $R_7$ is as defined above, then $R_6$ and $-NR_8$ may, together with the carbon atoms of the ring to which $-NR_8$ and $R_6$ are attached, form a 4 to 8 inclusive membered saturated or unsaturated ring which may contain 0, 1 or 2 further hetero atoms, which ring carries substituents selected from the values of $R_3$ to $R_6$, save that when $-NR_8$ forms parts of a double bond with an adjacent carbon atom, $R_7$ has no significance, $R_1$ and $R_2$, together with the ring carbon atoms to which they are attached, form a benzene ring, which ring carries substituents $R_9$ to $R_{12}$, $R_3$ to $R_6$ and $R_9$ to $R_{12}$, which may be the same or different, are each hydrogen, halogen, phenoxy, alkyl, fluoroalkyl, alkanoyl, benzoyl, $RS(O)_n-$, $-NO_2$, $-NR_{16}R_{17}$, $-NHCOR$, $-COOH$ or an ester or amide thereof, or alkoxy optionally substituted by phenyl, and in addition, an adjacent pair of $R_3$ to $R_6$ carried on ring A or an adjacent pair of $R_9$ to $R_{12}$ may together form a chain $-(CH_2)_x-$ or, together with the carbon atoms to which they are attached, form a 6 membered carbocylic or nitrogen heterocyclic ring, n is 0, 1 or 2, x is 3, 4 or 5, X is S, O or $NR_{18}$, $R_{18}$ is hydrogen, $-COR$, $-COOR$ or alkyl which latter is optionally substituted by $-OCOR$ or by phenyl, R, $R_{16}$ and $R_{17}$, which may be the same or different, are each hydrogen, phenyl, or alkyl optionally substituted by phenyl, the phenyl groups in turn optionally being substituted by alkyl, provided that (a) at least one of $R_3$ to $R_5$ or $R_9$ to $R_{12}$ is other than hydrogen when y is 0, W is $-NR_7R_8$, X is $NR_{18}$ where $R_{18}$ is hydrogen, A represents a benzene ring and, (i) $R_7$ has no significance, and $R_6$ and $-NR_8$, together with the carbon atoms of the ring to which $-NR_8$ and $R_6$ are attached, form a 6 membered fully unsaturated, unsubstituted ring containing no further heteroatoms, or when (ii) $R_6$, $R_7$ and $R_8$ are all hydrogen, and (b) W is not $-NR_7R_8$ save when y is 0 or when $R_6$ and $-NR_8$, together with the carbon atoms of the ring to which $-NR_8$ and $R_6$ are attached, form a 4 to 8 inclusive membered unsaturated ring which contains, 0, 1 or 2 further heteroatoms, which ring carries substituents selected from the values of $R_3$ to $R_6$, and when y is 0, ring A is fully unsaturated, none of $R_3$ to $R_6$ nor $R_9$ to $R_{12}$ are selected from phenoxy, fluoroalkyl, alkanoyl, $-NHCOR$ or alkoxy substituted by phenyl, nor do an adjacent pair or $R_3$ to $R_6$ form a $-(CH_2)_x$ chain;

X is not $NR_{18}$ where $R_{18}$ is $-COR$, $-COOR$ or alkyl substituted by phenyl, R is not phenyl substituted by alkyl, $R_{16}$ and $R_{17}$ are not phenyl substituted by alkyl nor alkyl substituted by phenyl, n is 0, and W is a 5 or 6 membered fully unsaturated heterocyclic ring containing a nitrogen atom ortho to the point of attachment of ring A, which ring carries substituents selected from the values of $R_3$ to $R_6$, then in addition to the values given above, $R_1$ and $R_2$ may each be hydrogen, alkyl or may, together with the ring carbon atoms to which they are attached, form a pyridine ring, which ring carries substituents selected from the values of $R_9$ to $R_{12}$, ring A may be a 5 membered fully unsaturated carbocyclic ring or a 5 or 6 membered fully unsaturated oxygen containing heterocyclic ring, M may be an O, S or N atom, $R_3$ to $R_6$ when carried on ring A or ring W may be alkoxy substituted by —OH, or by an optionally protected oxo group, an adjacent pair of $R_3$ to $R_6$ when carried on ring A may, together with the ring carbon atoms to which they are attached, form a 5 membered fully unsaturated carbocyclic or nitrogen containing heterocyclic ring, or a 5 or 6 membered fully unsaturated O or S containing heterocyclic ring, each ring carrying substituents selected from the values of $R_3$ to $R_6$, an adjacent pair of $R_3$ to $R_6$ carried on ring W may, together with the ring carbon atoms to which they are attached, form a 5 or 6 membered fully unsaturated carbocyclic or O, S or N containing heterocyclic ring carrying substituents selected from the values of $R_3$ to $R_6$, an adjacent pair of $R_9$ to $R_{12}$, together with the ring carbon atoms to which they are attached, may form a 5 membered carbocyclic or nitrogen containing heterocyclic ring or a 5 or 6 membered O or S containing heterocyclic ring, and $R_{16}$ and $R_{17}$ may, together with the nitrogen atom to which they are attached, form a 5 or 6 membered saturated ring which may contain a further heteroatom, and pharmaceutically acceptable salts thereof.

According to the invention we also provide a process for the production of a compound of formula I, or a pharmaceutically acceptable salt thereof, which comprises (a) selective oxidation of a compound of formula I in which p is 0 to a corresponding compound of formula I in which p is 1, (b) modification of a compound of formula I containing one or more groups convertible to a group, —NH$_2$, —CH$_2$OH, or C=O, to a compound of formula I containing a group —NH$_2$, —CH$_2$OH or C=O, (c) reaction of a compound of formula I in which X is NR$_{18}$ where R$_{18}$ is hydrogen with a compound R$_{19}$Z in which R$_{19}$ is as defined for R$_{18}$ above, save that it cannot be hydrogen, and Z is a good leaving group, (d) reaction of a compound of formula III,

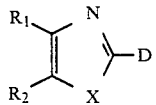

in which $R_1$, $R_2$ and X are as defined above, with a compound of formula IV,

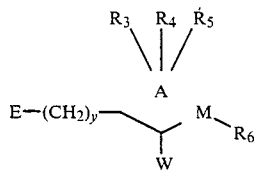

in which $R_3$, $R_4$, $R_5$, $R_6$, y, W, M and A are as defined above, and one of D and E is —SH or S$^-$ and the other is a good leaving group, or (e) for the production of a compound of formula I, in which W is a fully unsaturated ring containing a nitrogen atom ortho to the point of attachment of ring A, reaction of a compound of formula V,

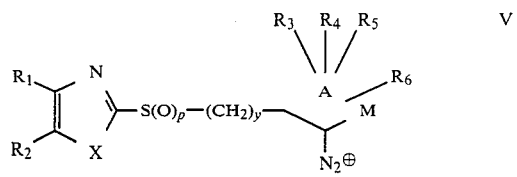

in which $R_1$ to $R_6$, p, y, M, X and A are as defined above with a compound of formula IIb,

in which B is a 5 or 6 membered fully unsaturated heterocyclic ring carrying substituents selected from the values of $R_3$ to $R_6$, and where desired or necessary converting the resulting compound of formula I to a pharmaceutically acceptable salt thereof, or vice versa.

The selective oxidation of process (a) may be carried out in a solvent which is inert under the reaction conditions, e.g. ethyl acetate, dichloromethane, chloroform or a mixture thereof. The reaction is preferably carried out at less than room temperature, e.g. $-20°$ to $+20°$ C. Suitable oxidising agents for use in the reaction are hydrogen peroxide; peracids, e.g. m-Chloroperbenzoic acid; or t-butylhydroperoxide in the presence of a suitable catalyst, e.g. vanadyl acetyl acetonate, or periodates, e.g. sodium periodate in aqueous alcohol, e.g. methanol.

The modification of one group to another of process (b) may be selective reduction, e.g. —NO$_2$ to —NH$_2$ or HC=O to CH$_2$—OH, or selective hydrolysis, e.g. of a protected carbonyl group to C=O. The selective reduction of —NO$_2$ to NH$_2$ may, for example, be carried out chemically under basic conditions, e.g. using hydrazine and Raney nickel, but is preferably carried out using hydrogen and a catalyst, e.g. PtO$_2$ in ethanol, as the reaction medium. The selection reduction of CH=O to CH$_2$OH may be carried out, for example using sodium borohydride. The selective hydrolysis is preferably carried out in an aqueous solution under acidic conditions.

In process (c) the good leaving group may be, for example, halogen (chlorine or iodine), and the reaction may be carried out in a solvent or solvent mixture which is inert under the reaction conditions, e.g. dimethyl formamide, in the presence of a base, e.g. potassium carbonate and at a temperature in the range 15°–35° C., e.g. at 20°–25° C.

For process (d) the good leaving group may be a sulphone, e.g. —SO$_2$Me, or a halogen, e.g. chlorine or bromine. The reaction may be carried out in any suitable solvent, e.g. N,N-dimethylformamide, N,N-dimethyl acetamide or methanol, at an optionally elevated temperature and may take place in the presence of a catalyst, e.g. Cu or an acid acceptor, e.g. potassium carbonate. We prefer D to be a good leaving group and E to be SH or S—.

The reaction of process (e) may be carried out in any suitable solvent, e.g. water, and at a temperature in the range 50°–100° C., e.g. at about 80°.

The compounds of formula III may be made from known compounds using conventional techniques known per se, for example, those compounds of formula III in which X is $NR_{18}$, where $R_{18}$ is H, and D is SH or $S^-$ may be made, for example, by reacting a compound of formula VII,

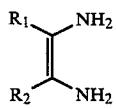

VII in which $R_1$ and $R_2$ are as defined above, with $CS_2$. The reaction is preferably carried out under nitrogen and at a temperature in the range 50°–80° C. Those compounds of formula III in which D is a sulphone, e.g. $-SO_2Me$, may be made from the corresponding thiol compound, e.g. by reaction first with methyl iodide and potassium carbonate in dimethyl formamide at a temperature in the range 0°–50° C. followed by treatment with Oxone (Registered Trade mark of the DuPont Co, peroxymonosulphate) in aqueous methanol at a temperature in the range 0°–50° C.

The compounds of formula IV may be made from known compounds using conventional techniques known per se, for example, those compounds of formula IV in which E is $-SH$ or $S^-$, y is O and W is a ring of formula IIb, may be made using the following route:

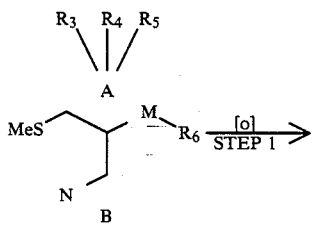

VIII

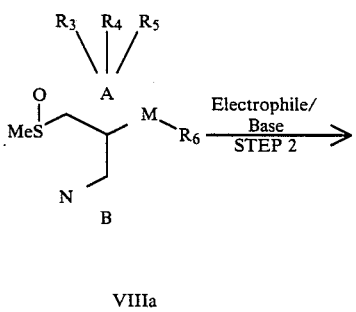

VIIIa in which $R_3$ to $R_6$, M, A and B are as defined above.

The oxidation of step 1 may be carried out as described for process (a) above. Step 2 may be carried out, for example, with trifluoroacetic acid and triethylamine in methanol. Under oxidizing conditions (e.g. in the presence of air) a disulphide may be a bi-product of step 2. The disulphide may be converted to the corresponding sulphide by reduction. Suitable reagents for this reduction are sodium borohydride and sodium cyanoborohydride.

The compounds of formula VIII may be made by a coupling or cyclisation reaction reaction as shown below.

(a) Coupling

Reaction of a compound of formula IX

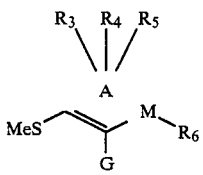

IX in which $R_3$ to $R_6$, M, and A are defined above and G is a metal ion (e.g. lithium) or a Grignard reagent (e.g. MgBr), with a compound of formula IIa or its N-oxide or ortho halo (e.g. o-fluoro) derivative,

IIa in which B is as defined above.

(b) Cyclisation

Reaction of a compound of formula X

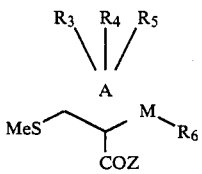

X in which $R_3$ to $R_6$, M and A are as defined above, and Z is a good leaving group, e.g. chloro, with, for example, (i) when ring B is pyridine, $CH_3-C(O)-CH=CH-OMe$, followed by $NH_3$, or (ii) when ring B is imidazole, $NH_2C(R_7)=C(R_{21})NH_2$, in which $R_{20}$ and $R_{21}$ are selected from the values of $R_3$ to $R_6$ above.

The compounds of formula V may be made by diazotisation of a compound of formula I, in which W is $-NR_7R_8$ where $R_7$ and $R_8$ are both hydrogen.

The diazotisation may be carried out in any suitable solvent, e.g. water, in the presence of acid, e.g. hydrochloric acid, at a temperature in the range 0°–15° C., e.g. below 5° C., and with an alkali metal nitrite, e.g. sodium nitrite.

The compounds of formulae IIb, IIa, VII, IX and X are either known or may be made by conventional processes known per se.

The compounds of formula I, and the intermediates therefor, may be isolated from their reaction mixtures using conventional techniques.

Certain of the compounds of formulae IV, VIII and VIIIa are novel and we provide these novel compounds for use as intermediates in the synthesis of compounds of formula I as defined above.

In particluar compounds of formula IVa,

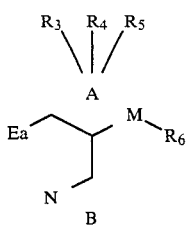

in which $E_a$ is SH, S−, SMe or SOMe, ring A is a benzene or thiophen ring, M is a carbon or sulphur atom, $R_3$ to $R_6$ are as defined above and ring B is either a pyridine ring carrying substituents selected from the values of $R_3$ to $R_6$ as defined above, save that an adjacent pair of $R_3$ to $R_6$ cannot, together with the carbon atoms to which they are attached, form a ring or ring B and an adjacent pair of the substituents selected from the values of $R_3$ to $R_6$ which it carries form a 1-isoquinolinyl, 2-imidazo[1,2-a]pyridine or 2-N-alkylated-benzimidazoyl group, which group carries substituents selected from the values of $R_3$ to $R_6$, are novel and are provided for use as intermediates in the synthesis of compounds of formula I as defined above.

Pharmaceutically acceptable salts of the compounds of formula I include salts with suitable organic or inorganic acids, e.g. with a hydrohalic, sulphuric, alkanesulphonic, tartaric or citric acid. We also provide, when the compound of formula I carries a —COOH, or other acidic group, salts with suitable organic or inorganic bases, e.g. ammonium, alkali metal, alkaline earth metal, alkylamino, etc. salts. The benzimidazole nucleus itself is acidic and can form salts with appropriate bases as above.

We also provide the compounds of formula I, without proviso (a) (i), and pharmaceutically acceptable salts thereof, for use as pharmaceuticals, e.g. for use as cytoprotective agents, in the treatment or prophylaxis of inflammatory conditions, as mucosa protectants, or in the prevention or inhibition of gastric acid secretion.

The compounds of formula I, and pharmaceutically acceptable salts thereof, are useful because they possess pharmacological activity in animals; in particular they are useful because they have cytoprotective properties, are useful in the treatment or prohylaxis of inflammatory situations and/or to prevent or inhibit gastric acid secretion, e.g. in the test set out in Am. J. Physiol., 1982, 243(6), G505–510. The compounds of formula I are also useful as intermediates in the synthesis of other chemicals.

The new compounds are thus indicated for use in the prevention or inhibition of gastric acid secretion, and/or conditions normally involving excess gastric acid secretion, e.g. peptic, duodenal, gastric, recurrent or stormal ulceration, dyspepsia, duodenitis, Zollinger-Ellison syndrome, reflux oesophagitis and the management of haemorrhage, e.g. from erosion of ulcers in the upper gastrointestinal tract, especially when a major blood vessel is not involved. The compounds may also be used to treat gastritis or dyspepsia associated with administration of non-steroidal anti-inflammatory drugs, in the prophylaxis of gastrointestinal haemorrhage from stress ulceration in seriously ill or burned patients, in the prophylaxis of recurrent haemorrhage in patients with bleeding peptic ulcers, before general anaesthesia in patients at risk of acid aspiration syndrome (Mendelson's syndrome) and to reduce the chance of haemorrhage in patients with leukaemia, graft versus host disease or with severe hepatic failure. The above conditions may be treated whether or not they are associated with excess gastric acid secretion.

The compounds may also be used to treat cholera, paratyphus, tourist diarrhoea, toxin-induced diarrhoea and local gastric catarrh.

The new compounds are also indicated for use as cytoprotective agents, especially for the gastrointestinal tract, and can be utilized for the treatment or prevention of a non-gastric-acid-induced, non-traumatically-induced, non-neoplastic gastrointestinal inflammatory disease for example, Crohn's disease, inflammatory bowel disease, infectious enteritis, colitis, ulcerative colitis, pseudomembranous colitis, diverticulitis, and allergenic and radiological inflammatory diseases.

The compounds are also indicated for use in the treatment or prophylaxis of inflammatory conditions in mammals, including man, especially those involving lysozymal enzymes. Conditions that may be specifically mentioned are: rheumatoid arthritis, gout, eczema, polyserositis and allergic alveolitis.

Patterns of therapeutic use which may be mentioned are:

(a) a high dose initially, for say 2–4 weeks, followed by lower-dose maintenance therapy after the condition has improved, e.g. the ulcer has healed, (b) as in (a) above, but the maintenance therapy includes another cytoprotective agent, e.g. a $PGE_2$ derivative, (c) combination therapy, using a low dose of the compound of the invention in association with a low, well-tolerated dose of another cytoprotectant and/or antacid, (d) intermittent dosing, e.g. every second day, may be appropriate as maintenance therapy.

For the above mentioned uses the dosage administered will, of course, vary with the compound employed, the mode of administration and the treatment desired. However, in general, satisfactory results are obtained when the compounds are administered at a dosage of from $10^{-6}M$ to $10^{-4}M$ in the test set out in Am. J. Physiol, 1982, 243 (6), G505–G510. For man the indicated total daily dosage is in the range of from about 1 mg to 3,000 mg, preferably 5 to 500 mg, and more preferably from about 10 mg to 200 mg, which may be administered in divided doses from 1 to 6 times a day or in sustained release form. Thus unit dosage forms suitable for administration comprise from about 1.0 mg to 600 mg of the compound admixed with a solid or liquid pharmaceutically acceptable diluent, carrier or adjuvant.

The compounds of formula I, and pharmaceutically acceptable salts thereof, have one or more of the following advantages. They are more readily absorbed, have increased bioavailability, are more stable around neutral pH, are less irritant to the GI tract, are more specific in action, have less toxic side effects, are more rapidly activated by acid, e.g. gastric acid, are more stable to acid, e.g. gastric acid, produce more advantageous results, e.g. in the 'Shay Rat Test' as described by H. Shay et al in Gastroenterology, 5 43–61 (1945), or have other advantageous properties when compared to known compounds of similar structure.

We prefer ring A to be fully unsaturated. When ring A is a heterocyclic ring we prefer it to contain one heteroatom. Specific groups ring A may represent include furan, pyrazole, pyrimidine, pyridine, benzene or thiophen. We prefer ring A to be a benzene or thiophen ring. When ring A is a pyridine ring it may be joined to the —S(O)$_n$ group in the 4 position and to ring B in the 3 position, or it may be joined to the —S(O)$_n$ group in the 3 position and to ring B in the 2 position. When ring A is a thiophen ring it may be joined to the —S(O)$_n$ group at the 2 position and to the ring B at the 3 position or it may be joined to the —S(O)$_n$ group at the 3 position and to the ring B at the 2 position.

When W is a 5 or 6 membered nitrogen containing heterocyclic ring, that ring may contain 1 or 2 further heteroatoms and preferably 1 or 2 further nitrogen atoms. We prefer that ring to be a ring of formula IIb. We particularly prefer that ring to be a pyridine or imidazole ring. When that ring is an imidazole ring it may be joined to ring A at its 2 or 4 position. When that ring is an imidazole ring it may be N-substituted, e.g. N-alkylated. When that ring is an imidazole ring joined to ring A at its 2 position we prefer it to be an N-methylated imidazole.

Specific groups $R_7$ and $R_8$ which may be mentioned include hydrogen, methyl and phenyl.

When $R_7$ and $R_8$, together with the nitrogen atom to which they are attached, form a ring, the ring may be saturated or unsaturated and may contain a further nitrogen, oxygen and/or sulphur atom, e.g. it may be a piperidino or morpholino ring.

When A is a benzene ring, and W is $NR_7R_8$ where $R_7$ and $R_8$ are each hydrogen or alkyl C1 to C6, we prefer ring A to carry, in addition to the group $NR_7R_8$, a substituent —$NR_{16}R_{17}$ preferably positioned para to the $NR_7R_8$ group. We prefer the group —$NR_{16}R_{17}$ to be —$NH_2$ or —$N(CH_3)_2$.

When W is $NR_7R_8$ and $R_6$ and —$NR_8$, together with the carbon atoms of the ring to which $R_6$ and —$NR_8$ are attached, form a ring, that ring may be an imidazole, pyridine, pyrrole or piperidino ring, e.g. an N-methyl piperidino ring, or preferably a pyridine ring. When $R_6$ and —$NR_8$ form a pyridine ring, as described above, we prefer ring A to be a benzene ring, y to be 0 and X to be $NR_{18}$. When $R_6$ and —$NR_8$ form a pyridine ring as described above, we prefer that ring to have a substituent selected from the values of $R_3$ to $R_6$ other than hydrogen para to the nitrogen of the group —$NR_8$. We prefer that substituent to be selected from alkoxy, phenoxy, benzyloxy, —$NR_{16}R_{17}$, —$RS(O)_n$, where n is O, or alkyl C 1 to C6. We particularly prefer the substituent para to the ring nitrogen atom to be alkoxy, e.g. methoxy.

L may be, for example, —$CH_2CH_2$—, —CH=, —$CH_2CH$= or preferably —$CH_2$—.

Specific groups —$LNR_9R_{10}$ which may be mentioned include —$CH_2N(CH_3)Ph$, —CH=N—$NR_{22}R_{23}$, —$CH_2NH$—$N(CH_3)_2$ and —CH=N—$OR_{24}$, in which $R_{22}$, $R_{23}$ and $R_{24}$, which may be the same or different, are each hydrogen, alkyl C 1 to C6 or phenyl.

We prefer y to be 0.

We prefer X to be $NR_{18}$.

$R_{18}$ may be methyl, —$CO_2CH_2Ph$, or preferably hydrogen.

We prefer p to be 1.

When any of $R_3$ to $R_6$ or $R_9$ to $R_{12}$ is halogen, it may be chlorine or fluorine.

When any of $R_1$ to $R_{21}$ or R represent or contain a carbon containing group we prefer that group to contain up to and including 10, and preferably up to and including 6, carbon atoms.

When any of $R_3$ to $R_6$ or $R_9$ to $R_{12}$ represent an ester we prefer it to be derived from a C 1 to C6 alcohol, e.g. to be a methyl or ethyl ester.

When any of $R_3$ to $R_6$ or $R_9$ or $R_{12}$ represents an amide they may be, for example, an unsubstituted or a mono- or di-alkyl C1 to C6 substituted amide.

The number of substituents $R_3$ to $R_6$ or $R_9$ to $R_{12}$ clearly cannot be more than the number of positions available for substitution on the ring to which they are attached.

Specific groups $R_3$, $R_4$, $R_5$ and $R_6$ include hydrogen, methyl, ethyl, chloro, —$NHCOCH_3$, —$NO_2$, —$NR_{20}R_{21}$, methoxy, ethoxy, propyloxy, isopropyloxy, ethoxy substituted by OH, by an oxo group and by a protected oxo group, e.g. a ketal, in particular ethylene dioxy.

When an adjacent pair of $R_3$ to $R_6$, together with the ring carbon atoms to which they are attached, form a ring we prefer that ring to be a carbocyclic ring and more particularly to be a benzene ring. When an adjacent pair $R_3$ to $R_6$, which are carried on a ring W, form a ring as described above, we prefer ring W to be a pyridine or imidazole ring. We particularly prefer that when an adjacent pair $R_3$ to $R_6$, which are carried on a ring W, form a ring as described above, they form with ring W a 1-isoquinolinyl, 2-imidazo[1,2-a]pyridine or more particularly a 2-benzimidazolyl group, which groups carry substituents selected from the values of $R_3$ to $R_6$ above. Specific examples of such substituents include hydrogen, halogen (e.g. chloro) or alkoxy.

We prefer $R_1$ and $R_2$, together with the ring carbon atoms to which they are attached, to form a benzene ring.

Specific groups $R_9$, $R_{10}$, $R_{11}$ and $R_{12}$ include hydrogen, methyl, methoxy, ethoxy, chlorine, —$NO_2$, $CF_3$, p-toluenesulphonyl, —$NR_{20}R_{21}$, benzoyl, methoxycarbonyl, ethoxycarbonyl and phenylcarbonyl.

When an adjacent pair or $R_9$ to $R_{12}$ form a 5 or 6 membered ring it may be saturated, partially unsaturated or fully unsaturated and may contain 0, 1 or 2 heteroatoms. We prefer that ring to be carbocyclic or to be an oxygen containing heterocyclic ring. We particularly prefer that ring to be a benzene or 1,3 dioxolan ring.

We prefer $R_9$ to $R_{12}$ to be selected from hydrogen, alkyl or alkoxy.

Specific groups $R_{16}$ and $R_{17}$ include hydrogen, methyl and phenyl.

When $R_{16}$ and $R_{17}$, together with the nitrogen atom to which they are attached, form a ring containing a further heteroatom, we prefer that heteroatom to be oxygen, When $R_{16}$ and $R_{17}$, together with the nitrogen atom to which they are attached, form a ring we prefer that ring to be a pyrrolidino or morpholino ring.

When $R_1$ and $R_2$ form a benzene ring, y is 0, A is a benzene ring and W is a pyridine ring, we prefer at least one of the substituents $R_3$ to $R_6$, carried on ring A, ring W or on a ring formed by an adjacent pair of substituents, to be selected from alkyl, $RS(O)_n$ where n is 0, —$NR_{16}R_{17}$ or alkoxy optionally subtituted by hydroxy or by an optionally protected oxo group. More specifically to be selected from methyl, ethyl, methoxy, ethoxy, propyloxy, isopropyloxy, ethoxy substituted by OH, by an oxy group or by a protected oxo group, or —$NR_{16}R_{17}$ where $R_{16}$ and $R_{17}$ represent methyl, phenyl or, together with the nitrogen atom to which they are attached, form a pyrrolidino or morpholino ring.

When ring A is a benzene ring attached to the —S(O)$_n$ group in the 2 position and to ring W in the 1 position, we particularly prefer the substituent in the 4 position (i.e. para to the position of attachment of ring W) to be selected from alkyl, RS(O)$_n$ where n is 0, —NR$_{16}$R$_{17}$ or alkoxy optionally substituted by hydroxy or by an optionally protected oxo group.

When ring W is a pyridine ring attached to ring A in the 2 position, we prefer the substituent in the 4 position (i.e. para to the ring N atom) to be selected from alkyl, RS(O)$_n$ where n is 0, —NR$_{16}$R$_{17}$ or alkoxy optionally substituted by hydroxy or by an optionally protected oxo group.

We particularly prefer compounds of formula I in which R$_1$ and R$_2$, together with the ring carbon atoms to which they are attached, form a benzene ring which benzene ring carries substituents R$_9$, R$_{10}$, R$_{11}$ and R$_{12}$, X is NR$_{18}$, R$_{18}$ is hydrogen, y is 0, p is 1, A is a benzene ring and W is a ring of formula IIb in which ring B is a pyridine ring having a substituent para to the ring N atom selected from alkyl, RS(O)$_n$ where n is 0, —NR$_{16}$R$_{17}$ or alkoxy optionally substituted by hydroxy or by an optionally protected oxy group or for ring B to be an imidazole ring attached to ring A in the 2 position and in which the substituents in the 4 and 5 positions, together with the ring carbon atoms to which they are attached, form a benzene ring which benzene ring carries subtituents selected from the values of R$_3$ to R$_6$.

Specific groups of compounds of formula I include

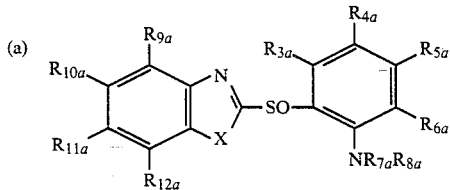

(a)  Ia in which R$_{3a}$, R$_{4a}$, R$_{5a}$, R$_{6a}$, R$_{9a}$, R$_{10a}$, R$_{11a}$ and R$_{12a}$, which may be the same or different, are each hydrogen, halogen, alkoxy, alkyl, fluoroalkyl, alkanoyl, RS(O)$_n$, —NO$_2$, —NR$_{16}$R$_{17}$, —NHCOR, or —COOH or an ester or amide thereof, or an adjacent pair of R$_{3a}$, R$_{4a}$, R$_{5a}$, R$_{6a}$, R$_{9a}$, R$_{10a}$, R$_{11a}$ and R$_{12a}$ may, in addition to the values given above, together form a chain —(CH$_2$)$_x$—or, together with the carbon atoms to which they are attached, form a 6 membered unsaturated carbocylic or nitrogen heterocyclic ring, x, n, X, R$_{16}$, R$_{17}$ and R are as defined above, R$_{7a}$ and R$_{8a}$, which may be the same or different, are each hydrogen, alkyl, phenyl or cycloalkyl each of which may optionally be substituted by phenyl, the phenyl group in turn optionally being substituted by alkyl, or one of R$_{7a}$ and R$_{8a}$ may be as defined above and the other may be —OR$_{13}$ or —NR$_{14}$R$_{15}$, or R$_{7a}$ and R$_{8a}$, together with the nitrogen atom to which they are attached, may form a saturated or unsaturated 4 to 8 inclusive membered ring which may contain 0, 1 or 2 further hetero atoms, which ring may carry one or more substituents R$_{3a}$ to R$_{6a}$, and R$_{13}$, R$_{14}$ and R$_{15}$ are as defined above, or R$_{7a}$ is as defined above save that it cannot form a ring with R$_{8a}$, and R$_{6a}$, and R$_{8a}$, together with the nitrogen atom and the carbon atoms of the ring to which the nitrogen atom and R$_{6a}$ are attached, form a saturated 4 to 8 inclusive membered ring which may contain 0, 1, or 2 further hetero atoms, which ring may carry one or more substituents R$_{3a}$ to R$_a$, with the proviso (a) (ii) above,

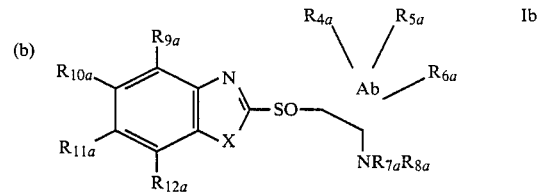

(b)  Ib in which R$_{4a}$ to R$_{6a}$, R$_{7a}$ and R$_{8a}$, R$_{9a}$ to R$_{12a}$ and X are as defined above, and A$_b$ represents a 5 or 6 membered nitrogen or sulphur containing heterocyclic ring which is connected to the rest of the molecule through a ring carbon atom,

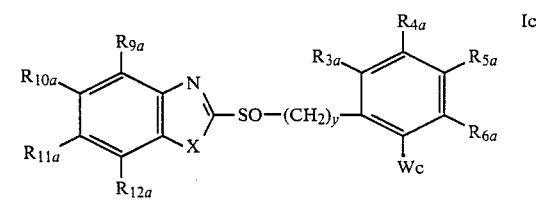

(c)  Ic in which R$_{3a}$ to R$_{6a}$, R$_{9a}$ to R$_{12a}$, y and X are as defined above, W$_c$ is a group —L$_c$NR$_{7c}$R$_{8c}$ or is a 5 or 6 membered heterocyclic ring containing a nitrogen atom ortho or meta to the point of attachment to the rest of the molecule.

R$_{7c}$ and R$_{8c}$, which may be the same or different, are each hydrogen, alkyl, phenyl or cycloalkyl each of which may optionally be substituted by phenyl, the phenyl groups in turn optionally being substituted by alkyl, or one of R$_{7c}$ and R$_{8c}$ is as defined above and the other is —OR$_{13}$ or —NR$_{14}$R$_{15}$, or R$_{7c}$ and R$_{8c}$, together with the nitrogen atom to which they are attached, may form a saturated or unsaturated 4 to 8 inclusive membered ring which may contain 0, 1 or 2 further hetero atoms, which ring may carry one or more substitutents R$_{3a}$ to R$_{6a}$, and R$_{13}$, R$_{14}$ and R$_{15}$ are as defined above, L$_c$ is a group containing 1 or 2 carbon atoms inclusive, optionally linked to the nitrogen atom by a double bond in which case R$_{7c}$ has no significance,

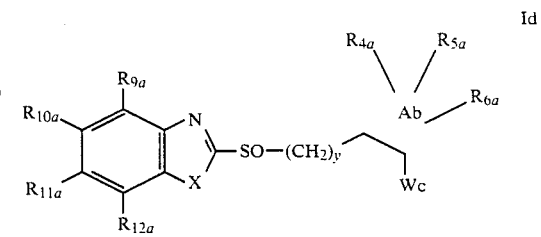

(d)  Id in which R$_{4a}$ to R$_{6a}$, R$_{9a}$ to R$_{12a}$, W$_c$, A$_b$, X and y are as described above, (e) 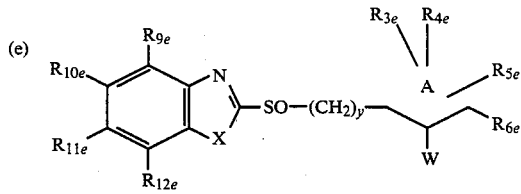 Ie in which A, y and W are as defined above, $R_{3e}$ to $R_{6e}$ and $R_{9e}$ to $R_{12e}$, which may be the same or different, are each hydrogen, halogen, phenoxy, alkyl, fluoroalkyl, alkanoyl, $RS(O)_n$, —$NO_2$, —$NR_{16}R_{17}$, —NHCOR, —COOH or an ester or amide thereof, or alkoxy optionally substituted by phenyl, and in addition, an adjacent pair of $R_{3e}$ to $R_{6e}$ or $R_{9e}$ to $R_{12e}$ may together form a chain —$(CH_2)_x$—or, together with the carbon atoms to which they are attached, form a 6 membered carbocylic or nitrogen heterocyclic ring, R, $R_{16}$, $R_{17}$, n and x are as defined above, X is S, O or $NR_{15}$, $R_{15}$ is hydrogen, —COR, —COOR or alkyl which latter is substituted by —COR, with the provisos (a) (i), (a) (ii) and (b) above, (f) 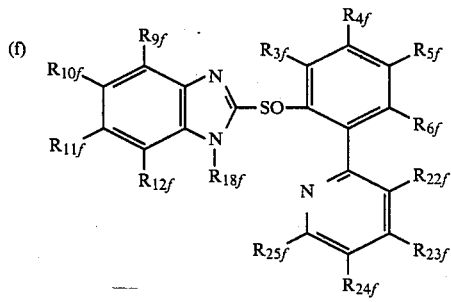 If in which at least one of $R_{3f}$, $R_{4f}$, $R_{5f}$, $R_{6f}$, $R_{22f}$, $R_{23f}$, $R_{24f}$ and $R_{25f}$ is selected from alkyl, alkoxy, or —$NR_{16f}R_{17f}$, and the remainder of $R_{3f}$ to $R_{6f}$ and $R_{23f}$ to $R_{25f}$ are each hydrogen, halogen, —$NO_2$, or —COOH or an ester or amide thereof, $R_{9f}$, $R_{10f}$, $R_{11f}$ and $R_{12f}$, which may be the same or different, are each hydrogen, halogen, alkyl, alkoxy, —$NO_2$, —$NR_fR_{26f}$ or —COOH or an ester or amide thereof, $R_{18f}$ is hydrogen or alkyl optionally substituted by —OCOR $R_f$ and $R_{26f}$, which may be the same or different, are each hydrogen, phenyl, or alkyl, $R_{16f}$ and $R_{17f}$, which may be same or different, are hydrogen, alkyl, phenyl or may, together with the nitrogen atom to which they are attached, form a 5 or 6 membered saturated ring, which ring may contain a further heteroatom, (g) 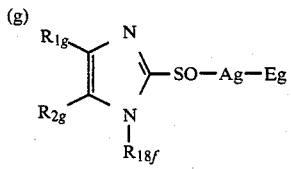 Ig in which $A_g$ represents a 5 or 6 membered nitrogen, oxygen or sulphur containing fully unsaturated heterocyclic ring which is connected to the —SO— group through a ring carbon atom, and which may be fused to a benzene ring, $E_g$ represents a 5 or 6 membered nitrogen containing fully unsaturated heterocyclic ring, which may be fused to a benzene ring, $R_{1g}$ and $R_{2g}$, which may be the same or different, are each hydrogen or alkyl, or may, together with the carbon atoms to which they are attached, form a benzene or pyridine ring which in turn may be substituted by one or more substituents selected for the values of $R_{9f}$ to $R_{12f}$ defined above, $R_{18f}$ is as defined above, (h) 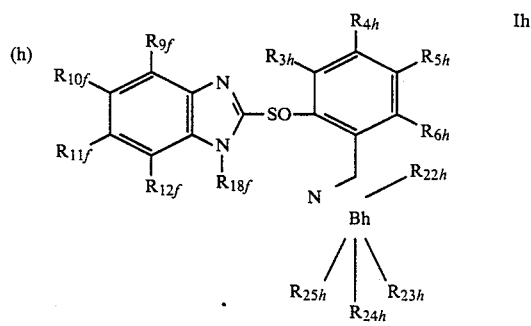 Ih in which at least one adjacent pair of $R_{22h}$, $R_{23h}$, $R_{24h}$ and $R_{25h}$, together with the ring atoms to which they are attached, form a 5 or 6 membered fully unsaturated carbocyclic or heterocyclic ring, and the remainder of $R_{22h}$ to $R_{25h}$ are as defined for $R_{3f}$ to $R_{6f}$ above, $B_h$ is a 5 or 6 membered fully unsaturated nitrogen containing heterocyclic ring, $R_{18f}$, $R_{9f}$, $R_{10f}$, $R_{11f}$ and $R_{12f}$ are as defined above, $R_{3h}$, $R_{4h}$, $R_{5h}$ and $R_{6h}$ have the significances given for $R_{3f}$ to $R_{6f}$ above and, in addition, an adjacent pair of $R_{3h}$, $R_{4h}$, $R_{5h}$ and $R_{6h}$ may, together with the ring atoms to which they are attached, form a 5 or 6 membered fully unsaturated carbocyclic or heterocyclic ring, (i) 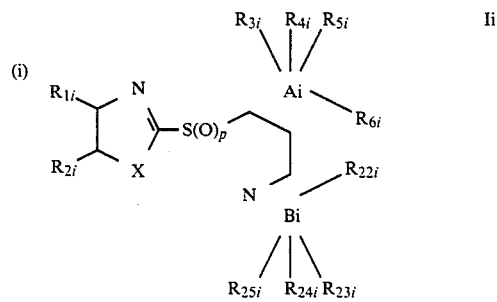 Ii in which $A_i$ is a 5 or 6 membered, fully unsaturated, carbocyclic or heterocyclic ring, $B_i$ is a 5 or 6 membered, fully unsaturated, nitrogen containing heterocyclic ring carrying substituents selected from the values of $R_{3i}$ to $R_{6i}$, X is $NR_{18i}$, O or S, $R_{18i}$ is hydrogen or alkyl optionally substituted by —OCOR, p is 0 or 1, $R_{3i}$, $R_{4i}$, $R_{5i}$ and $R_{6i}$, $R_{22i}$, $R_{23i}$, $R_{24i}$ and $R_{25i}$, which may be the same or different, are selected from hydrogen, alkyl, halogen, —$SR_i$, benzoyl, —$NO_2$, —$NR_{16i}R_{17i}$, —COOH or an ester or amide thereof, or alkoxy optionally substituted by hydroxy or by an optionally protected oxo group, or in addition to the values above an adjacent pair of $R_{3i}$ to $R_{6i}$ or $R_{22i}$ to $R_{25i}$ may, together with the ring atoms to which they are attached, form a 5 or 6 membered, fully unsaturated, carbocyclic or heterocyclic ring which carries substituents $R_{27i}$, $R_{28i}$, $R_{29i}$ and $R_{30i}$, $R_{27i}$, $R_{28i}$, $R_{29i}$ and $R_{30i}$, which may be same or different, are selected from hydrogen, alkyl, alkoxy, halogen, —$SR_i$, benzoyl, —$NO_2$, —$NR_{16i}R_{17i}$ or —$CO_2H$ or an ester or amide thereof, save when ring $A_i$, ring $B_i$ or the ring formed by an adjacent pair of $R_{3i}$ to $R_{6i}$ or $R_{22i}$ to $R_{25i}$ is 5 membered, then respectively $R_{6i}$, $R_{25i}$ or $R_{30i}$ has no significance, $R_{1i}$ and $R_{2i}$, which may be the same or different, are selected from hydrogen or alkyl or may, together with the ring carbon atoms to which they are attached, form a benzene or pyridine ring, which ring carries subtituents $R_{9i}$, $R_{10i}$, $R_{11i}$ and $R_{12i}$, $R_{9i}$, $R_{10i}$, $R_{11i}$ and $R_{12i}$, which may be the same or different, are selected from hydrogen, alkyl, halogen, —$SR_i$, benzoyl, alkoxy, —$NO_2$, —$NR_{16i}R_{17i}$ or —$CO_2H$ or an ester or amide thereof, or in addition to the values above an adjacent pair of $R_{9i}$, $R_{10i}$, $R_{11i}$ and $R_{12i}$ may, together with the ring carbon atoms to which they are attached, form a 5 or 6 membered, carbocyclic or heterocyclic ring, $R_{16i}$ and $R_{17i}$, which may be the same or different, are selected from hydrogen, alkyl, phenyl or may, together with the nitrogen atom to which they are attached, form a 5 or 6 membered, saturated ring, which ring may contain a further heteroatom, $R_i$ is hydrogen, phenyl or alkyl optionally substituted by phenyl, provided that when $R_{1i}$ and $R_{2i}$, together with the ring carbon atoms to which they are attached, form a benzene ring, $A_i$ is a benzene ring and $B_i$ is a pyridine ring, then at least one or $R_{3i}$ to $R_{6i}$, $R_{22i}$ to $R_{25i}$ and $R_{27i}$ to $R_{30i}$ is selected from alkyl, —$SR_i$, —$NR_{16i}R_{17i}$ or alkoxy optionally substituted by hydroxy or by an optionally protected oxo group.

According to our invention we also provide a pharmaceutical composition comprising (preferably a minor proportion of) a compound of formula I, or a pharmaceutically acceptable salt thereof, as active ingredient, in admixture with a pharmaceutically acceptable adjuvant, diluent or carrier. Examples of suitable adjuvants, diluents or carriers are: for tablets and dragees; lactose, starch, talc or stearic acid; for capsules, tartaric acid or lactose; for suppositories, natural or hardened oils or wax; and for injections (i.m. or i.v.) or enemas water, surfactants and preservatives. The compounds may also be administered transdermally, e.g. in an ointment base. The compound of formula I, or the pharmaceutically acceptable salt thereof, preferably has a mass median diameter of from 0.01 to 10 microns. The compound of such particle size may be made by grinding or milling followed if necessary by particle size classification using, for example, a sieve. The compositions may also contain suitable preserving, stabilising, and wetting agents, solubilizers, sweetening and colouring agents and flavourings. The compositions may, if desired, be formulated in sustained release form.

The compounds may, if desired, be co-administered, with (e.g. as a mixture with) an antacid buffer.

We prefer compositions which are designed to be taken by ingestion or rectally and to release their contents in the intestine. We particularly prefer compositions which will pass through the acidic parts of the gastrointestinal tract unaffected, e.g. enteric coated formulations.

Some of the compounds of formula I are optically active and may be resolved into their optical isomers using conventional techniques known per se. The invention therefore provides the compounds as their optical isomers, or as mixtures, e.g. racemic mixtures, thereof.

The compounds of formula I may exist in tautomeric forms and these tautomeric forms are included in the definition of the compounds of formula I. In particular when X is $R_{18}$ and $R_{18}$ is hydrogen the imidazole nucleus may exist in tautomeric forms.

The invention is illustrated, but in no way limited, by the following Examples in which temperatures are in degrees centigrade.

EXAMPLE 1

2-(1H-Benzimidazol-2-yl sulphinyl)-N,N-dimethyl benzenamine (a) 2-(N,N-Dimethylamino)-phenyldisulphide 2-Aminophenyldisulphide (10 g) was suspended in water (42 ml) and sodium bicarbonate (28 g) added. The mixture was stirred vigorously with ice bath cooling while dimethylsulphate (28.3 ml) was added dropwise over 10 minutes. The mixture was heated to 60° and stirred overnight. The cooled mixture was made strongly basic with sodium hydroxide solution and stirred for two hours. The mixture was diluted with water and extracted with ethyl acetate. The ethyl acetate was washed with water and brine, and then dried and evaporated. The resulting brown oil was triturated with 40°–60° petroleum ether which produced fine crystals. The crystals were filtered and dried affording 7.11 g of the desired product.

NMR (CDCl$_3$) delta 7.50(m 2H) 7.10(m 6H) 2.81(s 12H).

(b) 2-(1H-Benzimidazol-2-yl thio)-N,N-dimethyl benzenamine

To a stirred solution of the product of step (a) (2.0 g) in dry tetrahydrofuran (100 ml) was added a solution of lithium aluminium hydride (20 ml of 1M in ether) dropwise. After 1 hour water was added dropwise. When the vigorous effervescence had ceased the mixture was poured onto water and made acidic with dilute hydrochloric acid. After shaking, the solution was basified with sodium bicarbonate and extracted with ethyl acetate. The ethyl acetate was washed with water and brine, and then dried and evaporated to leave a clear oil (1.52 g). The oil was stirred under nitrogen with 2-chlorobenzimidazole (1.4 g) in dry degassed dimethylformamide (50 ml) at 80° for 1 hour. The cooled mixture was poured into an aqueous sodium bicarbonate solution and the product extracted with ethyl acetate. The ethyl acetate was washed with brine, and then dried and evaporated. The residue was crystallised from ethyl acetate to afford the sub-title compound as prisms 670 mg, mp 148°–9°.

(c) 2-(1H-Benzimidazol-2-yl sulphinyl)-N,N-dimethyl benzenamine

The product of step (b) (4.1 g) was dissolved in ethyl acetate (130 ml) and the stirred solution cooled to −10°. An ice cold solution of m-chloroperbenzoic acid (2.77 g of 95%) in ethyl acetate (20 ml) was added. The resulting solution was stirred for 40 minutes, and then washed with sodium bicarbonate solution, water and brine, dried and evaporated. The residue was purified by flash chromatography to produce a colourless foam. The foam was subjected to high vacuum which afforded 3.18 g of the title compound.

NMR (CDCl$_3$) delta 11.86 (broad s 1H) 7.77 (d.o.d.), 7.74 (broad 2H), 7.43(m 2H), 7.25(m 2H), 7.19 (d.o.d. 1H), 7.13(m 1H), 2.90(s 6H).

EXAMPLE 2

By the method described in Example 1, and using the appropriate starting materials, may be prepared the following compounds:

(a)
  (i) 2-(Benzimidazol-2-yl thio)-N,N-dimethyl-4-methoxy benzenamine mp 150°–153°.
  (ii) 2-(1H-Benzimidazol-2-yl sulphinyl)-N,N-dimethyl-4-methoxy benzenamine mp 178°–9°.

(b)
  (i) 2-(5-Chloro-1H-benzimidazol-2-yl thio)-N,N-dimethyl benzenamine mp 152°.
  (ii) 2-(5-Chloro-1H-benzimidazol-2-yl sulphinyl)-N,N-dimethyl benzenamine mp 132°–3° (dec).

(c)
  (i) 2-(5-Nitro-1H-benzimidazol-2-yl thio)-N,N-dimethyl benzenamine mp 78°–80°.
  (ii) 2-(5-Nitro-1H-benzimidazol-2-yl sulphinyl)-N,N-dimethyl benzenamine mp 180°–181°.

(d)
  (i) 2-(5-Chloro-1H-benzimidazol-2-yl thio)-4-methoxy-N,N-dimethyl benzenamine mp 138°–9°.
  (ii) 2-(5-Chloro-1H-benzimidazol-2-yl sulphinyl)-4-methoxy-N,N-dimethyl benzenamine
  NMR (CDCl$_3$) delta:11.6 (broad, 1H), 7.3 (m,5H), 6.95 (dod,1H), 3.68 (s,3H), 2.72 (s,6H).

(e)
  (i) 2-(1H-Benzimidazol-2-yl thio)-4-(1-methylethoxy-N,N-dimethyl benzenamine mp 172°–3°.
  (ii) 2-(1H-Benzimidazol-2-yl sulphinyl)-4-(1-methylethoxy-N,N-dimethyl benzenamine mp 172°–3°.

(f)
  (i) 2-(5,6-Dichloro-1H-benzimidazol-2-yl thio)-4-methoxy-N,N-dimethyl benzenamine mp 207°–8°.
  (ii) 2-5,6-Dichloro-1H-benzimidazol-2-yl sulphinyl)-4-methoxy-N,N-dimethyl benzenamine mp 164°–5°.

(g)
  (i) Methyl 2-(2-dimethylamino-5-methoxyphenyl thio)-1H-1H-benzimidazole-5-carboxylate m/z 357, 190(base peak), 171, 169.
  (ii) Methyl 2-(2-dimethylamino-5-methoxyphenyl sulphinyl)-1H-benzimidazole-5-carboxylate
  C$_{18}$H$_{19}$O$_4$SN$_3$: Found C, 57.49; H, 5.11; N, 10.88; S, 8.59; H$_2$O, 0.2% (Karl-Fischer) 0.2% water requires: C, 57.84; H, 5.1; N, 11.23; S, 8.55%.

EXAMPLE 3

2-(5-Chloro-1H-benzimidazol-2-yl sulphinyl)benzenamine (a) 2-(5-Chloro-1H-benzimidazol-2-yl thio)benzenamine 2-(5-Chloro-1H-benzimidazol-2-yl thio)nitrobenzene (0.3 g) was dissolved in dry ethanol (100 ml) with warming and the solution was hydrogenated in the presence of 10% Pd/C at 3 atmospheres pressure and 50° for 2.75 hours. The heating and stirring were stopped and the mixture was left standing under an H$_2$ atmosphere overnight. The mixture was then filtered through a filter aid and evaporated under reduced pressure, and dried under vacuum at 50° to leave the subtitle compound as a pale greenish glassy solid (0.23 g), mp 155°–156°.

(b) 2-(5-Chloro-1H-benzimidazol-2-yl sulphinyl) benzenamine

The product of step (a) (5.1 g) in dichloromethane (150 ml) stirring in an ice bath (approx. 5°) was treated dropwise with 95% m-chloroperbenzoic acid (3.51 g) in dichloromethane (80 ml). The mixture was stirred in the ice bath for 2 hours and then poured onto saturated aqueous sodium bicarbonate solution. The organic layer was separated, washed, dried and evaporated under reduced pressure to leave 4.61 g of creamish/grey glassy solid. This was taken up in a small volume of CH$_2$Cl$_2$/ethyl acetate 9/1 and the insoluble material filtered off, washed with petroleum ether (30°–40°) and dried under vacuum at 50° to give 2.63 g of the desired product, mp 176°–178°.

EXAMPLE 4

By the method of Example 3, and using appropriate starting materials, may be prepared the following compounds:

(a)
  (i) 2-(5-Methoxy-1H-benzimidazol-2-yl thio) benzenamine mp 61°–64°.
  (ii) 2-(5-Methoxy-1H-benzimidazol-2-yl sulphinyl) benzenamine mp 73°–75°.

(b) p1 (i) 2-(5,6-Dimethoxy-1-H-benzimidazol-2-yl thio) benzenamine mp 79°–80°.
  (ii)
  2-(5,6-Dimethoxy-1H-benzimidazol-2-yl sulphinyl)-benzenamine
  C$_{15}$H$_{15}$O$_3$SN$_3$: Found: C, 56.08; H, 4.89; N, 12.66; S, 9.62%; Required: C, 56.78; H, 4.73; N, 13.25; S, 10.09%.

EXAMPLE 5

N-[2-(1H-Benzimidazol-2-yl sulphinyl)phenylmethyl]-N-methyl-benzenamine (a) N,N'-Dimethyl-N,N'-(2,2'-diphenyl methyldithio)-bis-benzenamine Di-(2-chloromethylphenyl)disulphide (7.4 g) and N-methyl benzenamine (11.77 g) were heated at 100° in dry dimethylformamide (200 ml) for 72 hours. The reaction mixture was poured into water and extracted into ether. The organic phase was washed with water, dried and evaporated. The residue was chromatographed (SiO$_2$/3:1 petroleum ether-ethyl acetate) to afford the sub-title compound (4.2 g). Mass spectrum M+ 456. Base Peak (BP) 228.

(b) N-[2-(1H-Benzimidazol-2-yl thio)phenylmethyl]-N-methyl-benzenamine

The product of step (a) was converted into the subtitle compound by the method of Example 1 (b), mp 168°–9°.

(c) N-[2-(1H-Benzimidazol-2-yl subphinyl)phenylmethyl]-N-methyl-benzenamine

The product of step (b) was converted into the title compound by the method of Example 1 (c), mp 164°–6°.

EXAMPLE 6

2-(1-Methyl-1H-benzimidazol-2-yl sulphinyl)benzenamine 2-(1H-Benzimidazol-2-yl sulphinyl)benzenamine (850 mg, 3.31 mmole) in dimethylformamide (16 ml) and methyl iodide (515 mg, 3.63 mmole) were stirred at room temperature for 6 hours in a stoppered flask in the presence of potassium carbonate (1.66 g, 12 mmole). The mixture was poured into water and extracted with ethyl acetate (3×). The combined extracts were washed with water (3×), dried (anhydrous sodium sulphate) and evaporated to give a pale grey solid which was triturated with ether to give the title compound as an off-white solid (0.78 g; 87%), mp 146°–8°(-dec).

EXAMPLE 7

By the method of Example 6, and using the appropriate starting materials, were made the following compounds:
(a)
(i) 2-(1-Methyl-1H-benzimidazol-2-yl sulphinyl)-N,N-dimethyl benzenamine mp 143°–4°.
(ii) 2-(5,6-Dichloro-1-methyl-1H-benzimidazol-2-yl sulphinyl)-4-methoxy-N,N-dimethyl benzenamine mp 132°–3° containing 2.35% water (Karl-Fischer analysis).

EXAMPLE 8

2-(5-Amino-1H-benzimidazol-2-yl sulphinyl)-N,N-dimethyl benzenamine 2-(5-Nitro-1H-benzimidazol-2-yl sulphinyl)-N,N-dimethylbenzenamine (the product of Example 2 (c) (3g) was suspended in ethanol (300 ml), and hydrogenated at 1 atmosphere at room temperature, using platinium oxide as catalyst, for 3 days.

The catalyst was filtered off and solvent evaporated to give a yellow solid.

Purification by flash chromatography (silica, ethyl acetate: $CH_2Cl_2$; 2:1) gave the title compound, 1.01 g (37%), mp 178°.

EXAMPLE 9

2-(1H-Benzimidazol-2-yl sulphinyl)-N,N,N',N'-tetramethyl-1,4-benzenediamine (a)
N,N,N',N'-tetramethyl-2,5-diaminophenyldisulphide 2-Amino-5-N,N-dimethylaminophenylthiosulphonic acid )22.6 g) was stirred with sodium bicarbonate (46 g) and water (70 ml) until effervescence had ceased. Dimethyl sulphate (43 ml) was added and the mixture heated at 60° for 5 hrs. to the cooled mixture 880 ammonia (10 ml) was added and the mixture stirred for 30 mins. The mixture was concentrated in vacuo and treated with a solution of diazobicylco[2.2.2.]octane (31 g) in ethanol (100 ml) and the resulting mixture heated under reflux for 2 hrs. The solvent was removed in vacuo and the residue treated with conc. hydrochloric acid (60 ml). The mixture was heated at 90° for 45 mins. The cooled mixture was poured onto sodium bicarbonate (100 g) and after addition of water (100 ml) was extracted with ethyl acetate. The ethyl acetate was washed with water and brine and then dried and evaporated. The residue was flash chromatographed to produce the desired compound as an orange oil (3.1 g) NMR ($CDCl_3$) delta 7.03(1H)d, 6.95(1H)d, 6.50(1H)d.o.d., 2.78(6H)s, 2.73(6H)s.

(b) 2-(1H-Benzimidazol-2-yl thio)-N,N,N',N'-tetramethyl-1,4-benzenediamine

N,N,N',N'-tetramethyl-2,5-diaminophenyldisulphide (1.5 g) was dissolved in dry tetrahydrofuran (70 ml) and treated with an ethereal solution of lithium aluminium hydride (5.8 ml of 1M) dropwise over 20 mins. The solution was stirred for a further 40 mins. Water (100 ml) was added, dropwise initially until all vigorous effervescence had ceased, then more rapidly. The mixture was poured onto dilute hydrochloric acid and after mixing the solution was basified with sodium bicarbonate solution and extracted with ethyl acetate. The ethyl acetate was washed with brine, and then dried and evaporated to leave a clear oil 1.2 g. The oil was taken up in dry degassed dimethylformamide (50 ml) and a solution of 2-chlorobenzimidazole (930 mg) in dry degassed dimethylformamide (50 ml) was added. The mixture was stirred under nitrogen and heated to 80° for 2 hrs. The cooled mixture was poured onto water (200 ml) and basified with sodium bicarbonate solution. The precipitate was collected, washed well with water and then dried to afford the desired compound as a colourless solid (1.61 g) NMR ($CDCl_3$) delta 7.4 (broad 2H), 7.18(2H)m, 7.14(1H)d, 7.00(1H)d, 6.71(1H)d.o.d., 2.90(6H)s, 2.86(6H)s.

(c) 2-(1H-Benzimidazol-2-yl sulphinyl)-N,N,N',N'-tetramethyl-1,4-benzenediamine

The product of step (b) above (1.5 g) was dissolved in ethyl acetate (120 ml) and cooled to −10°. A solution of m-chloroperbenzoic acid (980 mg of 85%) in ethyl acetate (30 ml) was added in one portion and the mixture stirred for 1 hr. The mixture was filtered and the residue taken up in dichloromethane. The dichloromethane was washed with sodium bicarbonate solution, sodium metabisulphite solution, water and brine and then dried and evaporated. Flash chromatography afforded the title compound as an off white solid (857 mg) mp 213°–215° (NMR ($CDCl_3$) delta 7.7 (broad), 7.4 (2H)broad, 7.20(2H)m, 7.12(2H)m, 6.69(1H)d.o.d., 2.79 (6H) 2.60(6H)s.

EXAMPLE 10

2-(4-Methoxyquinolin-8-yl sulphinyl)-1H-benzimidazole (a) 8-(1H-Benzimidazol-2-yl thio)-1,4-dihydro-quinolin-4-one 8,8'-Dithio bis (4-methoxyquinoline) (2.5 g) was suspended in dry tetrahydrofuran (100 ml) at room temperature under nitrogen and treated with lithium aluminium hydride in ethereal solution (15 mmole). After 2 hours water was added dropwise followed by dilute HCl and after 10 minutes the mixture was basified with NaHCO₃ solution. This suspension was extracted into ethyl acetate, which was washed with brine, then dried and evaporated in vacuo. The residue was dissolved in dry degassed dimethylformamide (40 ml) containing 2-chlorobenzimidazole (2.3 g) and heated at 80° for 18 hours. The solution was poured into water (600 ml) and the precipitate collected and washed with water. Trituration with boiling $CH_2Cl_2$ afforded the sub-title product as a yellow powder 1.2 g, mp greater than 240°.

(b) 2-(4-Methoxyquinolin-8-yl thio)-1H-benzimidazole

The product of step (a) above (2.1 g) was reacted with $POCl_3$ (50 ml) at gentle reflux for 1 hour, then cooled, and cautiously poured onto ice (500 ml), then neutralised with ammonia. The precipitate was collected and dried, then a solution of sodium (483 mg) in dry methanol (25 ml) was added and the whole was refluxed for 36 hours. The mixture was cooled and treated with ammonium chloride, then evaporated in vacuo. The solid was extracted into ethyl acetate and the product was isolated by column chromatography ($SiO_2$/2:1 ethyl acetate/petroleum ether) to afford the sub-title compound 430 mg, mp 218°-9°.

(c) 2-(4-Methoxyquinolin-8-yl sulphinyl)-1H-benzimidazole

The product of step (b) above (390 mg) in ethyl acetate (20 ml) was cooled to −5° and treated with m-chloroperbenzoic acid (273 mg of 85% pure material). The temperature was allowed to rise to ambient. The reaction mixture was then diluted with ethyl acetate and methylene chloride, and then washed with sodium bisulphite solution, sodium bicarbonate solution and brine. The solution was dried and evaporated. Column chromatography ($SiO_2$/ethyl acetate) gave the title compound 140 mg, mp 178°-9° (d).

EXAMPLE 11

2-(4-Methoxyquinolin-8-yl methylsulphinyl)-1H-benzimidazole (a) 8-Bromomethyl-4-methoxyquinoline 4-Methoxy-8-methylquinoline (346 mg, 2 mmole), N-bromosuccinimide (365 mg, 2.05 mmole) and benzoyl peroxide (10 mg) in $CCl_4$ (8 ml) were heated under reflux for 2.5 hours. The mixture was cooled and the succinimide was filtered off. The filtrate was washed with dilute aqueous NaHCO₃ (1×) and water (1×), dried ($Na_2SO_4$) and evaporated to yield the sub-title compound as a pale yellow solid which was recrystallised from petroleum ether/cyclohexane to give colourless needles.

Yield 195 mg (38.6%).

MW 251/3 (207), 172 (base peak), (157), (142), (129), (115), (102), (91), (76), (63), (51), (39).

(b) 2-(4-Methoxyquinolin-8-yl methylthio)-1H-benzimidazole

The product of step (a) above and 2-mercapto benzimidazole (3.0 g, 20 mmole) were stirred at room temperature in dry dimethylformamide (75 ml) with $K_2CO_3$ (5.5 g, 40 mmole) for 4 hours. The mixture was poured into water and extracted with $CHCl_3$ (3×). The combined extracts were washed with water (3×), dried ($Na_2SO_4$) and evaporated to yield a cream solid which was recrystallised from ethyl acetate and then dried in vacuo at room temperature, mp 189°-192°.

(c) 2-(4-Methoxyquinolin-8-yl methylsulphinyl)-1H-benzimidazole

The product of step (b) above was converted by a method analogous to that of Example 3 (b) to the title compound, mp 214° (d)).

EXAMPLE 12

By the method of Example 11, and with the appropriate starting materials, was made the following compound:

(a) (i) 2-(Quinolin-8-yl methylthio)-1H-benzimidazole mp 165°-6°.

(ii) 2-(Quinolin-8-yl methylsulphinyl)-1H-benzimidazole mp 207°-8°.

EXAMPLE 13

2-[2-(2-Pyridyl)-phenyl sulphinyl]-1H-benzimidazole (a) 2-[2-(2-Pyridyl)-phenyl thio]-1H-benzimidazole 2-(1H-Benzimidazol-2-yl thio)benzenamine (8.5 g) in dilute hydrochloric acid (680 ml) was cooled (0° to −5°) with stirring and sodium nitrite (2.68 g) in water (85 ml) was added dropwise, keeping the temperature below 0°. The resulting diazonium salt solution was stirred at 0° for 0.5 hours, then added portionwise to pyridine (800 ml) with stirring at 80° for 1 hour. The pyridine was distilled off, and replaced with 880 ammonia which was in turn distilled off. The residue was treated with water and extracted into dichloromethane, washed, dried, evaporated under reduced pressure and purified by flash column chromatography using dichloromethane:ethyl acetate, 9:2 as eluant to give 3.07 g of the sub-title product.

Elemental Analysis: Found: C,70.48, H,4.52, N,13.48, S,9.93, KF1.7% $C_{18}H_{13}N_3S$ 0.25H₂O, Required: C,70.20, H,4.39, N,13.66, S,10.43, KF,1.4%.

(b) 2-[2-(2-Pyridyl)-phenyl sulphinyl]-1H-benzimidazole

The product of step (a) above 2.0 g in dichloromethane (100 ml) was treated dropwise, stirring in an ice bath, with 95% m-chloroperbenzoic acid (1.31 g) in dichloromethane (50 ml) for 50 minutes. The reaction mixture was then poured onto a saturated aqueous sodium bicarbonate solution, extracted into dichloromethane, washed, dried and evaporated to leave a creamish solid. Trituration with petroleum ether (30° to 40°) and filtration give the title product as a cream solid, 1.89 g. M/S m/e 319 (M⁺, 45%), 186 (100%).

EXAMPLE 14

By the method of Example 13, and using the appropriate starting materials, were made the following compounds:

(a) (i) 5-Chloro-2-(2-(2-pyridyl)-phenyl thio)-1H-benzimidazole

M.S. m/e 337 (M⁺, 25%), 186 (100%).

(ii) 5-Chloro-2-(2-(2-pyridyl)-phenyl sulphinyl)-1H-benzimidazole

M.S. m/e 354/6 (M⁺+1) FAB m.s.

(b)

(i) 2-[2-(2-Pyridyl)-phenyl thio]-benzothiazole m/e 320 Base Peak 186.
(ii) 2-[2-(2-Pyridyl)-phenyl sulphinyl]-benzothiazole m/e Mwt+Base Peak 337 (M+1).

(c)
(i) Methyl 2-(2-(2-pyridyl)-phenyl thio)-1H-benzimidazole-5-carboxylate m/z (FAB) 361 M+.
(ii) Methyl 2-(2-(2-pyridyl)-phenyl sulphinyl)-1H-benzimidazole-5-carboxylate m/z (FAB) 378 (M+ +1).

(d)
(i) 4-Trifluoromethyl-2-[2-(2-pyridyl)-phenyl thio]-1H-benzimidazole mp 169°-171°.
(ii) 4-Trifluoromethyl-2-[2-(2-pyridyl)-phenyl sulphinyl]-1H-benzimidazole mp 224°-5°.

(e)
(i) 2-[2-(2-Pyridyl)-phenyl thio]-naphtho[2,3-d] imidazole m/z 353 (M+).
(ii) 2-[2-(2-Pyridyl)-phenyl sulphinyl]-naphtho [2,3-d]imidazole m/z (FAB) 370 (M+1).

(f)
(i) 2-[5-Chloro-2-(2-pyridyl)-phenyl thio]-5-methoxy-1H-benzimidazole m/z 367/369 (M+).
(ii) 2-[5-Chloro-2-(2-pyridyl)-phenyl sulphinyl-5-methoxy-1H-benzimidazole mp 113° (d).

(g)
(i) 5,6-Dimethyl-2-[2-(2-pyridyl)-phenyl thio]-1H-benzimidazole mp 196°-8°.
(ii) 5,6-Dimethyl-2-[2-(2-pyridyl)-phenyl sulphinyl]-1H-benzimidazole mp 219°-221°.

(h)
(i) 5-Methyl-2-[2-(2-pyridyl)-phenyl thio]-1H-benzimidazole m/z 317 (M+).
(ii) 5-Methyl-2-[2-(2-pyridyl)-phenyl sulphinyl]-1H-benzimidazole mp 110°.

(i)
(i) 5-(4-Methylphenylsulphonyl)-2-[2-(2-pyridyl)-phenyl thio]-1H-benzimidazole MW (fast atom bombardment) 426 (M+ +1).
(ii) 5-(4-Methylphenylsulphonyl)-2-[2-(2-pyridyl)-phenyl sulphinyl]-1H-benzimidazole MW (fast atom bombardment) 422 (M+ +1).

(j)
(i) N-[4-(4,7-dimethoxy-1H-benzimidazole-2-yl thio)-3-(2-pyridyl)-phenyl]acetamide
NMR delta (DMSO d6) 2.05 (3Hs), 3.82 (6Hs), 6.53 (1Hd), 6.62 (1Hd), 7.19 (1Hd), 7.42 (1Hm), 7.49 (1H dod), 7.7 (1Hd), 7.93 (2Hm), 8.7 (1Hd), 10.15 (1Hs), 13.01 (1H br s).
(ii) N-[4-(4,7-dimethoxy-1H-benzimidazol-2-yl sulphinyl)-3-(2-pyridyl)phenyl]acetamide mp 217°-219° (dec).

EXAMPLE 15

2-[2-(4-Methoxy-2-pyridyl)-phenyl sulphinyl]-1H-benzimidazole (a) 2-[2-(4-Methoxy-2-pyridyl)-phenyl thio]-1H-benzimidazole To an ice cold solution of 2-(1H-benzimidazol-2-yl thio)benzenamine (1.70 g) in dilute hydrochloric acid (11 ml) was added dropwise a solution of sodium nitrite (0.53 g) in water (5 ml), keeping the temperature below 0°. The reaction mixture was stirred at this temperature for 0.5 hours then added portionwise to a mixture of 4-methoxypyridine (42.40 g) and pyridine (0.57 g) stirring at 80° for 1 hour. The pyridines were distilled off, replaced with 880 ammonia which was in turn distilled off. The residue was treated with water, extracted into dichloromethane, washed, dried, evaporated and the residue was purified by flash column chromatography using ethyl acetate as eluant to give the sub-title product as a creamish foam, 0.20 g.
M.S. m/e 333 (M+, 10%), 300 (M+ −32, 8%), 216 (100%).

(b) 2-[2-(4-Methoxy-2-pyridyl)-phenyl sulphinyl]-1H-benzimidazole

The title compound was prepared, from the product of step (a) above (0.18 g) by the method of Example 13 (b), as a cream/yellow solid, 0.10 g.
M.S. m/e 350 (M+ +1), 154 (100%), FAB m.s.

EXAMPLE 16

2-[2-(2-Pyridyl)-phenyl methylsulphinyl]-1H-benzimidazole (a) 2-(2-Pyridyl)-benzenemethanol 2-Aminobenzylalcohol (10 g) was dissolved in concentrated hydrochloric acid (25 ml) and the solution diluted with water (20 ml). The solution was stirred at 0° and a solution of sodium nitrite (5.9 g) in water (20 ml) added dropwise. The mixture was stirred at 0° for 40 minutes. The solution was added dropwise to pyridine (92 ml) stirred at 80°. After stirring at 80° for 90 minutes the mixture was concentrated in vacuo and the residue heated with 880 ammonia (100 ml). The mixture was concentrated in vacuo and the residue slurried with water and extracted with ethyl acetate. The ethyl acetate was washed with brine, dried and evaporated. Flash chromatography produced the sub-title compound as a red oil (3.8 g). M.S. m/e 185 Base Peak 80.

(b) 2-[2-(2-Pyridyl)-phenyl methylthio]-1H-benzimidazole

To a stirred solution of the product of step (a) above (1.5 g) in dry benzene (50 ml) was added thionyl chloride (0.71 ml) dropwise. After stirring for 1 hour the solvent was removed in vacuo. The residue was dissolved in dry dimethylformamide (50 ml) and the solution treated with benzimidazole-2-thione (1.22 g) and potassium carbonate (2.24 g). The mixture was stirred for 4 hours then poured onto water (500 ml). After stirring for 30 minutes the precipitate was collected, washed with water and dried. Flash chromatography produced the sub-title compound as a dark brown glass (200 mg).
NMR (CDCl3) delta 14.13 broad, 10.00 broad (1H), 8.81 (d.o.d. 1H), 7.98 (t.o.d. 1H), 7.93 (d,1H), 7.0-7.8 (m,9H), 4.45 (s,2H).

(c) 2-[2-(2-Pyridyl)-phenyl methylsulphinyl]-1H-benzimidazole

The product of step (b) above (169 mg) in ethyl acetate (10 ml) was cooled to −10° and treated with an ice cold solution of m-chloroperbenzoic acid (108 mg of 85%) in ethyl acetate (1 ml). The mixture was stirred for 50 minutes then washed with sodium bicarbonate solution, sodium bisulphite solution, water and brine and then dried and evaporated. Flash chromatography produced the title compound as a colourless solid (95 mg), mp 148°-150°.

EXAMPLE 17

1-Methyl-2-[2-(2-pyridyl)-phenyl sulphinyl]-1H-benzimidazole

2-[2-(2-Pyridyl)-phenyl sulphinyl]-1H-benzimidazole (Example 13) (0.7 g) in dry dimethylformamide (50 ml), methyl iodide (0.34 g) and anhydrous potassium carbonate (1.1 g) were stirred at room temperature for 1.75 hours. The mixture was poured onto water, extracted into ethyl acetate, washed, dried and evaporated under reduced pressure to leave the title compound as a cream solid (0.55 g).

Elemental Analysis: Found: C,67.48; H,4.54; N,12.60; S,9.62, $C_{19}H_{15}N_3OS$ 0.25 $H_2O$; Requires: C,67.48; H,4.59; N,12.40; S,9.47.

EXAMPLE 18

5,6-Diethoxy-2-[2-(2-pyridyl)-phenyl sulphinyl]-1H-benzimidazole

(a) 2-(2-Bromophenyl)pyridine

2-Bromobenzenamine (18.77 g) in 50 ml of conc HCl and 50 ml of water, was cooled in an ice bath and treated dropwise with stirring with a solution of sodium nitrite (8.28 g) in water (35 ml). After the addition was complete, the mixture was stirred in the ice bath for a further 30 minutes and then added portionwise (over 5 minutes) to pyridine (275 ml) stirred in an oil bath at 80° C. The mixture was heated (at 80° C.) for a further 1 hour, when the excess of pyridine was distilled off under reduced pressure. The residue was basified (aqueous sodium hydrogen carbonate) and extracted with ethyl acetate (3×). The extracts were washed with water (2×), dried (sodium sulphate) and evaporated to give a dark oil, which was flash chromatographed on silica using methylene chloride/ethyl acetate (20/1) as eluant. Pure sub-title compound (6.56 g) was obtained as a dark brown oil.

m/z 235/233 (MW), 154 (Base Peak).

(b) 5,6-Diethoxy-2-[2-(2-pyridyl)-phenyl thio]-1H-benzimidazole 5,6-Diethoxy-2-mercaptobenzimidazole (1.0 g) was treated with powdered KOH (235 mg) in dimethylacetamide (15 ml). Half of the solvent was distilled off (to remove water). The mixture was cooled and the product of step (a) above (1.0 g was added. The mixture was heated under reflux for 20 hours, cooled, poured into water, and acidified with HCl and rebasified with sodium hydrogen carbonate solution (pH approx. 8).

The dark suspension was extracted with ethyl acetate (2×) and the extracts were washed with water (3×), filtered to remove some black insoluble material and dried (sodium sulphate) to give a dark oil which was flash chromatographed on silica. The sub-title compound was obtained as a brown oil 100 mg (6%) usind neat ethyl acetate as eluant.

m/z 391, 362, 186 (Base Peak).

(c) 5,6-Diethoxy-2-[2-(2-pyridyl)-phenyl sulphinyl]-1H-benzimidazole

The product of step (b) above was converted to the title compound by the method of Example 13 above, mp 194°–5°.

EXAMPLE 19

2-(5-Chloro-1H-benzimidazol-2-yl sulphinyl)-N,N,N',N'-tetramethyl-1,4-benzenediamine

(a) 2-(5-Chloro-1H-benzimidazole-2-yl thio)-N,N,N',N'-tetramethyl-1,4-benzenediamine N,N,N',N'-Tetramethyl-2,5-diaminophenyldisulphide (1.3 g) was dissolved in dry tetrahydrofuran (70 ml) and an ethereal solution of lithium aluminium hydride (5.0 ml of 1M) was added dropwise over 10 minutes. After stirring for 30 minutes, water was added dropwise until no further effervescence was observed. The mixture was poured onto dilute hydrochloric acid, basified with sodium bicarbonate solution and extracted with ethyl acetate. The ethyl acetate was washed with water and brine, and then dried and evaporated to leave a clear gum (940 g). The gum was dissolved in dry degassed dimethylformamide (50 ml) and a solution of 2,5-dichloro-1H-benzimidazole (0.9 g) in dry degassed dimethylformamide (30 ml) was added. The mixture was stirred and heated to 80° for 2 hours. The solvent was removed in vacuo and the residue triturated with water. The solid was collected and dissolved in dichloromethane. The solution was dried and the solvent removed in vacuo. Flash chromatography produced the sub-title compound as a gum wich solidified on standing (550 mg).

MS MW 346/8 Base Peak 194.

(b) 2-(5-Chloro-1H-benzimidazol-2-yl sulphinyl)-N,N,N',N'-tetramethyl-1,4-benzenediamine The product of step (a) above (550 mg) was dissolved in ethyl acetate (20 ml) and cooled to −10°. A solution of m-chloroperbenzoic acid (320 mg of 85%) in ethyl acetate (5 ml) was cooled to 0° and added to the above solution. After stirring at below 0° for 3 hours the solution was washed with sodium bicarbonate solution, sodium metabisulphite solution, water and brine, and then dried and concentrated in vacuo. The residue was flash chromatographed to produce a yellow gum. Trituration with ether and petroleum ether produced the title compound as a pale yellow solid (125 mg), mp 161°–3°.

EXAMPLE 20

Phenylmethyl 2-[2-(2-pyridyl)-phenyl sulphinyl]benzimidazole-1-carboxylate

(a) Phenylmethyl 2-[2-(2-pyridyl)-phenyl thio]benzimidazole-1-carboxylate

2-[2-(2-Pyridyl)-phenyl thio]-benzimidazole (0.825 mmole) in anhydrous dimethylformamide (15 ml) was treated under nitrogen with sodium hydride (0.90 mmole). The mixture was stirred for 20 minutes at room temperature, cooled to 5° and benzyl chloroformate (0.90 mmole) was added. The mixture was allowed to attain room temperature, then stirred for 18 hours after which it was poured into ice/water and extracted with ethyl acetate (2×15 ml). The combined extracts were washed with water, dried (MgSO₄), filtered and evaporated to an oil. The oil was flash chromatographed on silica gel using 10% ethyl acetate in dichloromethane as eluant to give the sub-title compound as a brown oil, MW 437 Base Peak 91.

(b) Phenylmethyl 2-[2-(2-pyridyl)-phenyl sulphinyl]benzimidazole-1-carboxylate

Phenylmethyl 2-[2-(pyridyl)-phenyl thio]benzimidazole-1-carboxylate (0.41 mmole) in dry dichloromethane (10 ml) was treated at 0° with a solution of m-chloroperbenzoic acid (0.48 mmole) in dichloromethane (5 cm³). The mixture was stirred for 3 hours at between 0° and 10° and then poured into aqueous sodium hydrogen carbonate. The organic phase was separated, dried (MgSO₄), filtered and evaporated to give a pale brown foam. The foam was taken up into dichloromethane and flash chromatographed (4/1 CH₂Cl₂/60:80 petroleum ether) to give the title compound as a yellow gum.

FAB MW 454 (+1).

EXAMPLE 21

2-[2-(2-Pyridyl)-phenyl sulphinyl]-benzoxazole (a) 2-[2-(2-Pyridyl)-phenyl thio]-benzoxazole 2-Mercapto benzoxazole (604 mg; 4 mmole) was reacted with 2-(2-bromophenyl)pyridine (936 mg; 4 mmole) in the presence of KOH (224 mg; 4 mmole) in N-methyl pyrrolidine (16 ml). The mixture was heated under reflux for 6 hours, worked up and flash chromatographed (silica), using ethyl acetate/petroleum ether (2/3) eluant to give the sub-title compound as a pale brown oil (52 mg; 4.3%).

m/z 304, 281, 277, 271, 186 (Base Peak), 154, 135.

(b) 2-[2-(2-Pyridyl)-phenyl sulphinyl]-benzoxazole

Oxidation of the sulphide from step (a) (50 mg; 0.164 mmole) in methylene chloride (5 ml) at 5° with m-chloroperbenzoic acid (35.5 mg of 85%; 30.2 mg; 0.175 mmole) gave, after work-up, a grey oil which was flash chromatographed (silica), using ethyl acetate/petroleum ether (½) eluant to give the main title compound as a pale green solid (13.7 mg; 26%), mp 145°.

EXAMPLE 22

By the method of Example 21, and with the appropriate starting materials, was made the following compound:

(a) (i) Phenyl [2-[2-(2-pyridyl)-phenyl thio]-1H-benzimidazol-5-yl]methanone.

MS M/E 407 Base Peak 186.

(ii) Phenyl [2-[2-(2-pyridyl)-phenyl sulphinyl]-1H-benzimidazol-5-yl]methanone.

MS - Fab M/E (+1) 424.

EXAMPLE 23

5-Nitro-2-[4-nitro-2-(2-pyridyl)-phenyl sulphinyl]-1H-benzimidazole (a) 5-Nitro-2-[4-nitro-2-(2-pyridyl)-phenyl thio]-1H-benzimidazole 2-[(2-Pyridyl)-phenyl thio]-1H-benzimidazole (1.0 g) was stirred at 5° in a glacial acetic acid (30 ml)/concentrated sulphuric acid (60 ml) mixture. Concentrated nitric acid (18 ml)/concentrated sulphuric acid (28 ml) mixture was then added over 45 minutes. The temperature was maintained at below 10° for a further 3 hours, and was then allowed to attain ambient temperature, at which it was stirred for 18 hours. The mixture was poured onto crushed ice (600 g) and the pH was adjusted to approximately 8 by the addition of sodium hydrogen carbonate. The pale yellow product was filtered and well washed with water and dichloromethane. It was then vacuum dried to give the sub-title compound (1.0 g).

MS MI 393 Base Peak 231.

(b) 5-Nitro-2-[4-nitro-2-(2-pyridyl)-phenyl sulphinyl]-1H-benzimidazole

A solution of the sulphide of step (a) above (1.15 mmoles) in methanol (70 ml)/dichloromethane (50 ml) was stirred at 10°. Solid m-chloroperbenzoic acid (80%; 1.38 mmoles) was added portionwise over 5 minutes. The solution was stirred at 10° for a further 30 minutes and then concentrated to approximately 25 ml. Silica gel (approximately 10 g) was added and the remaining solvent removed. Flash chromatography using dichloromethane containing 20% ethyl acetate as eluant gave a pale orange solid (0.20 g) which was slurried in dichloromethane (50 ml) and filtered to give the title compound as an off-white solid, mp 208°-9° (dec).

EXAMPLE 24

2-[4-Dimethylamino)-2-(4-methoxy-2-pyridinyl)phenyl sulphinyl]-1H-benzimidazole (a) 2-(2-Hydroxy-5-nitrophenyl)-4-methoxy pyridine 4-Nitrobenzenediazonium tetrafluoroborate (65.8 mmol) was added portionwise with stirring at room temperature to a solution of 4-methoxypyridine N-oxide (50 mmol) in acetonitrile (150 ml). The mixture was stirred overnight at room temperature, treated with triethylamine (100 mmol) and the brown solution was heated under reflux for 15 minutes.

The solvent was removed on a rotary evaporator and the residue flash chromatographed on silica and eluted with chloroform to give the sub-title compound.

(b) 2-(2-Hydroxy-5-nitrophenyl)-4-methoxypyridine N,N-dimethylthiocarbamate

The compound from step (a) above (24.2 mmol), N,N-dimethylaminothiocarbamoyl chloride (37 mmol) in dimethyl formamide (250 ml) were stirred rapidly in the presence of potassium carbonate (60 mmol) for 24 hours, adding more potassium carbonate (1 g) after 18 hours. The mixture was acidified (to pH4) with dilute hydrochloric acid and extracted with ethyl acetate (3 times). The combined extracts were washed with water (4 times), dried (anhydrous sodium sulphate) and evaporated to yield a brown solid, which was triturated with ether, and filtered to give the sub-title compound.

'HNMR (CDCl₃) delta (d), 8.61 (d,1H), 8.52 (d,1H), 8.28 (dd,1H), 7.33 (d,1H), 7.22 (d,1H), 6.65 (m,1H), 3.86 (S,3H), 3.38 and 3.26 (NMe₂ 6H).

(c) 2-(2-Mercapto-5-nitrophenyl)-4-methoxypyridine N,N-dimethylcarbamate

The compound from step (a) above (13.5 mmol) in 2,2'-oxybisethanol (130 ml) was heated under nitrogen at 175° for 2 hours. The mixture was cooled, poured into water and extracted with ethyl acetate (3 times). The combined extracts were washed with water (3 times), dried (anhydrous sodium sulphate) and evaporated to yield a dark brown oil, flash chromatographed on silica and crystallised on standing under ether in the freezer. The sub-title compound was filtered off and obtained as a yellow solid.

m/z (FAB) 334 (M+1), 289, 247, (base peak,bp) 72.

(d) 2-(5-Amino-2-mercapto)-4-methoxypyridine N,N-dimethylcarbamate

The compound from step (c) above (3.75 mmol) was hydrogenated at room temperature at 3.33 atmosphere for 6 days in the presence of 10% palladium on charcoal (150 mg) in ethanol (150 ml) as solvent. The mixture was filtered and evaporated to give the subtitle compound as a pale yellow foam.

m/z 303 (M+), 283, (bp) 231.

(e) 2-(5-N,N-dimethylamino-2-mercapto)-4-methoxypyridine N,N-dimethylcarbamate The compound from step (d) above (2.97 mmol) in acetonitrile (15 ml) and formaldehyde solution (2.4 ml approximately 30 mmol) were treated portionwise with sodium cyanoborohydride (7.1 mmol) and stirred with occasional addition of acetic acid (to maintain pH approximately 5). After the addition stirring was continued for 1 hour when the mixture was poured into dilute aqueous sodium hydrogen carbonate solution and extracted with ethyl acetate, dried (sodium sulphate), flash chromatographed on silica, eluted with ethyl acetate to give the title compound as a pale yellow solid.

m/z (small peak) 331, (bp) 259.

(f) Disulphide of 2-(5-N,N-dimethylamino-2-mercapto)-4-methoxypyridine

The compound from step (e) above (110 mg, 0.33 mmol) in methanol (3 ml) was heated under reflux in the presence of sodium hydroxide (0.4 mmol) for 8 hours. A further aliquot of NaOH (0.4 mmol) was added and heating was continued for 15 hours. The mixture was poured into water, acidified with dilute aqueous HCl and the pH was then brought back to 8 with dilute aqueous sodium hydrogen carbonate.

The aqueous solution was extracted with ethyl acetate (3 times) and the extracts washed with water (2 times), dried (anhydrous sodium sulphate) and evaporated to give the subtitle compound as a yellow oil.

m/z 259 (MW/Z), 244, 228.

(g) 2-[4-Dimethylamino-2-(4-methoxy-2-pyridinyl thio)]-1H-benzimidazole

2-Chlorobenzimidazole (700 mg) and the compound from step (f) above (1.2 g) were heated under reflux with sodium cyanoborohydride (290 mg) in isopropanol (33 ml) and acetic acid (7 ml) for 2 hours. The solvent was removed on a rotary evaporator and the residue treated with dilute aqueous sodium hydrogen carbonate and extracted with CHCl₃ in the usual way, dried (Na₂SO₄) and recrystallised from ethyl acetate to give the sub-title compound as a white solid, mp 218°–220°.

(h) 2-[4-Dimethylamino-2-(4-methoxy-2-pyridinyl sulphinyl)]-1H-benzimidazole The compound from step (g) above 2.39 mmol) in methylene chloride (40 ml) was treated portionwise with m-Chloroperbenzoic acid (500 mg of 85%, 2.46 mmol) at −10° with stirring over 15 minutes. Stirring was continued for a further 1 hour then the mixture was worked up to give, after trituration with ether, the title compound as a grey solid.

m/z FAB 393 (M+1), 275 (bp).

EXAMPLE 25
5-Methoxy-2-[2-(4-methoxy-2-pyridinyl)phenylsulphinyl]-1H-benzimidazole

(a) 4-Methoxy-2-(2-methylthiophenyl-pyridine

Under a nitrogen atmosphere 2-bromothioanisole (9.6 g) in dry ether (20 ml) was added dropwise to magnesium (1.15 g) in ether (5 ml) containing iodine (1 small crystal). The reaction was initiated by the addition of methyl magnesium iodide (0.1 ml of 3.0M in ether). The mixture was heated under reflux for 1.5 hours to afford a clear solution of the Grignard reagent (20 ml). 4-Methoxypyridine-N-oxide (2 g) in dry tetrahydrofuran (50 ml) was mechanically stirred and ethychloroformate (1.52 ml) added dropwise. The stirred mixture was cooled to −78° and treated with the above Grignard solution (7.5 ml). After stirring for 2 hours the mixture was allowed to warm up to room temperature. The mixture was poured onto dilute hydrochloric acid and washed with ethyl acetate. The ethyl acetate was extracted with dilute hydrochloric acid. The aqueous solution was washed with chloroform then basified and reextracted with ethyl acetate. The ethyl acetate was washed with brine then dried and evaporated to leave the subtitle compound as a pale brown oil MS MW 231 bp 216.

(b) 4-Methoxy-2-(2-methylsulphinylphenyl)-pyridine

The product of step (a) above (750 mg) in ethyl acetate (7 ml) was cooled to −10° and treated with a solution of m-Chloroperbenzoic acid (660 mg) in ethyl acetate (4 ml). After 1 hour the solution was washed with sodium bicarbonate solution, sodium bisulphate solution and brine then dried and evaporated. The residue was flash chromatographed (ethyl acetate) to produce the subtitle compound as a clear oil MS (FAB) M+1 at 248 bp 232.

(c) 5-Methoxy-2-[2-(4-Methoxy-2-pyridyl)phenylthio]-1H-benzimidazole

The product of step (b) above (180 mg) was treated with trifluoracetic anhydride (1.5 ml) and heated under reflux for 1 hour. The solvent was removed in vacuo and the residue treated with methanol (10 ml) and triethylamine (10 ml). The mixture was concentrated in vacuo and the residue taken up in dichloromethane. The solution was washed with ammonium chloride solution then dried and evaporated. The residue was taken up in dry dimethylformamide and 2-chloro-5-methoxy-1H-benzimidazole (133 mg) and potassium carbonate (101 mg) added. The mixture was heated at 90°–95° for 1 hour then poured onto water and extracted with ethyl acetate. The ethyl acetate was washed with water and brine then dried and evaporated. Flash chromatography gave the subtitle compound as a light pink foam MS MW 363 bp 216.

(d) 5-Methoxy-2-[2-(4-methoxy-2-pyridyl)phenylsulphinyl]-1H -benzimidazole

The product of step (c) above (103 mg) was dissolved in ethyl acetate (7.5 ml) and stirred at −10°. A solution of m-chloroperbenoic acid (58 mg of 85%) in ethyl acetate (0.5 ml) was added and the mixture stirred for 50 minutes. The solution was washed with sodium bicarbonate solution, sodium bisulphite solution, water and brine then dried and evaporated. After trituration with ether the solid was dried to afford the title compound. MS (FAB) M+1 at 380.

EXAMPLE 26

By methods analogous to those of Example 25, using the appropriate starting materials, the following compounds were prepared.

(a)
  (i) 2-[2-(4-Ethyl-2-pyridinyl)phenylthio]-1H-benzimidazole. MS M+ 331.
  (ii) 2-[2-(Ethyl-2-pyridinyl)phenylsulphinyl]-1H-benzimidazole, mp 169°–171°.

(b)
  (i) Methyl 2-[2-(4-methoxy-2-pyridinyl)phenylthio]-1H-benzimidazole-5-carboxylate MS MW 391.
  (ii) Methyl 2-[2-(4methoxy-2-pyridinyl)phenyl sulphinyl]-1H-benzimidazole-5-carboxylate MS (FAB) M+1 408 bp 232.

(c)
  (i) 5-Methyl-2-[2-(4-methoxy-2-pyridinyl)phenylthio]-1H-benzimidazole. MS M+ 347.
  (ii) 5Methyl-2-[2-(4-methoxy-2-pyridinyl)phenyl sulphinyl]-1H-benzimidazole, mp 110°.

(d)
  (i) 2-[2-(4-Methyl-2-pyridinyl)phenylthio]-benzoxazole. MS MW 318 bp 200.
  (ii) 2-[2-(4-Methyl-2-pyridinyl)phenylsulphinyl]-benzoxazole. mp 140°–144°.
via
  (iii) 4-Methyl-2-(2-methylthio phenyl)-pyridine. MS MW 215 bp 200.
  (iv) 4-Methyl-2-(2-methylsulphinyl phenyl)-pyridine. MS MW 231 bp 216.

(e)
  (i) 2-[2-(4-Methoxy-2-pyridinyl)phenylthio]-benzoxazole. MS M+ 334.
  (ii) 2-[2-(4-Methoxy-2-pyridinyl)phenylsulphinyl]-benzoxazole, mp 128°–140° (decomp).

(f)
  (i) 2-[5-Methoxy-2-(4-methyl-2-pyridinyl) phenylthio]-1H-benzimidazole. MS M+ 347.
  (ii) 2-[5-Methoxy-2-(4-methyl-2-pyridinyl)phenyl sulphinyl]-1H-benzimidazole, mp 180°–184°.

(g)
  (i) 2-[2-(4-[2-methyl-1,3-dioxolan-2-ylmethoxy]-2-pyridinyl)phenylthio]-1H-benzimidazole, mp 82°–3°.
  (ii) 2-[2-(4-[2-methyl-1,3-dioxolan-2-ylmethoxy-2-pyridinyl)phenylsulphinyl]-1H-benzimidazole. MS (FAB) M+1 436.

(h)
  (i) 2-[2-(4-Methoxy-2-pyridinyl)phenylthio-1H-naphth[2,3-d]imidazole MS M+ 383.
  (ii) 2-[2-(4-Methoxy-2-pyridinyl)phenylsulphinyl-1H-naphth[2,3-d]imidazole, mp 154°.

(j)
  (i) 5-Methoxy-2-[2-(4-methoxy-2-pyridinyl)-5-methoxy phenylthio]-1H-benzimidazole. MS (FAB) M+1 394 bp 246.
  (ii) 5-Methoxy-2-[2-(4-methoxy-2-pyridinyl)-5-methoxy phenylsulphinyl]-1H-benzimidazole. MS (FAB) M+1 410.
via
  (iii) 2-(4-Methoxy-2-pyridinyl)-5-methoxy phenyl disulphide. MS (EI) bp 246 (FAB) M+1 493 bp 246.

(k)
  (i) 2-[2-(1H-2-Benzimidazolylthio)phenyl]-N-methyl-N-phenyl-4-pyridinamine. MS M+ 408.
  (ii) 2-[2-(1H-2-Benzimidazolylsulphinyl)phenyl]-N-methyl-N-phenyl-4-pyridinamine, mp 142°.
via
  (iii) N-Methyl-2-(2-methylthio phenyl)-N-phenyl-4-pyridinamine, MS M+ 306.
  (iv) N-Methyl-2-(2-methylsulphinyl phenyl)-N-phenyl-4-pyridinamine. MS (FAB) M+ +1 323.

(l)
  (i) 2-[5-Methoxy-2-(2-pyridinyl)phenylthio]-1H-benzimidazole. MS M+333.
  (ii) 2-[5-Methoxy-2-(2-pyridinyl)phenylsulphinyl-1H-benzimidazole, mp 180°–183°.
via
  (iii) 2-(4-Methoxy-2-methylthio phenyl)pyridine. MS M+ 231.
  (iv) 2-(4-Methoxy-2-methylsulphinyl phenyl)pyridine. MS (FAB) M+ +1 248.

(m)
  (i) 1-[2-(2-(1H-2-Benzimidazolylthio)phenyl-4-pyridinyloxy]propan-2-one. MS M+ 375.
  (ii) 1-[2-(2-(1H-2-Benzimidazolylsulphinyl)phenyl-4-pyridinyloxy]propan-2-one, mp 222°–223°.
Via the compound of Example 2 (h)(i) by aqueous acidic hydrolysis.

(n)
  (i) 4-Methoxy-2-[2-(4-methoxy-2-pyridinyl)phenylthio]-1H-benzimidazol. MS M+363.
  (ii) 4-Methoxy-2-[2-(4-methoxy-2-pyridinyl)phenyl sulphinyl]-1H-benzimidazol, mp 104°.

(o)
  (i) 2-[2-(5-Methyl-2-pyridinyl)phenylthio]-1H-benzimidazole. MS M+ 317.
  (ii) 2-[2-(5-Methyl-2-pyridinyl)phenylsulphinyl-1H-benzimidazole, mp 241°–242°.

(p)
  (i) 2-[2-(4-methoxy-6-methyl-2-pyridinyl)phenylthio]-1H-benzimidazol, mp 121°.
  (ii) 2-[2-(4-methoxy-6-methyl-2-pyridinyl)phenyl sulphinyl]-1H-benzimidazol, mp 169°–171°.
via
  (iii) 1,4-Dihydro-2-methyl-6-(2-methylthio phenyl)pyridin-4-one. MS m/e 231 (m+) 216 (100%).
  (iv) 4-Chloro-6-methyl-2(2-methylthio phenyl) pyridine. MS m/e 249/251 (M+) 234 (100%).
  (v) 4-Methoxy-6-methyl-2(2-methylthio phenyl) pyridine. MS m/e 245 (M+) 230 (100%).

(q)
  (i) 2-[2-(3-Methyl-2-pyridinyl)phenylthio]-1H-benzimidazole. MS M+ 317.
  (ii) 2-[2-(3-Methyl-2-pyridinyl)phenylsulphinyl]-1H-benzimidazole, mp 98°–100°.

EXAMPLE 27

2-[(5-Methoxy-2-(4-methoxy-2-pyridinyl)phenylsulphinyl]-1H-benzimidazole (a)

O-(2-Bromo-5-methoxyphenyl)-N,N-dimethylthiocarbamate

2-Bromo-5-methoxyphenol (29 g) was dissolved in dry dimethyl formamide (100 ml) and cooled to 0°. Anhydrous potassium carbonate (21.7 g) was added and the mixture stirred for 15 minutes. A solution of dimethylthio carbamoyl chloride (22.1 g) in dry dimethylformamide (50 ml) was added and the mixture allowed to warm to room temperature. After stirring for 5 hours the mixture was poured onto water and extracted with ethyl acetate. The ethyl acetate was washed with water, dilute sodium hydroxide solution, again with water then dried and evaporated. Flash chromatography (10% ethyl acetate/petroleum ether) produced the subtitle compound as a colourless solid NMR(CDCl$_3$) d 7.45 (dod, 1H) 6.72(m,2H) 3.79 (s,3H) 3.48 (s,3H) 3.40 (s,3H).

(b) S-(2-Bromo-5-methoxyphenyl)-N,N-dimethylthiocarbamate

The product of step (a) above (32.5 g) was dissolved in diethylaniline (330 ml) and the solution heated under reflux for 4 hours. The cooled mixture was poured onto dilute hydrochloric acid and extracted with ethyl acetate. The ethyl acetate was washed with dilute hydrochloric acid, water and brine then dried and evaporated to leave a brown gum. Flash chromatography (10% ethyl acetate/petroleum ether) produced the subtitle compound as a brown solid. MW M+1 at 288/290 bp 72.

(c) 2-Bromo-5-methoxythiophenol

The product of step (b) above (200 mg) was dissolved in methanol (4 ml). Aqueous sodium hydroxide solution (1.4 ml of 10%) was added and the mixture heated under reflux in a nitrogen atmosphere for 2 hours. The mixture was cooled, poured onto dilute hydrochloric acid and extracted with ethyl acetate. The ethyl acetate was washed with water and brine then dried and evaporated to leave the subtitle compound as an oil MS MW 218/220 bp 218.

(d) 1-Bromo-4-methoxy-2-methylthiobenzene

The product of step (c) above (140 mg) was dissolved in dry dimethyl formamide (2 ml). Potassium carbonate (114 mg) was added followed by methyl iodide (47 ml). The mixture was stirred for 2 hours, poured onto water and extracted with ethyl acetate. The ethyl acetate was washed with water and brine then dried and evaporated to leave the subtitle compound as a pale brown oil MS MW 232/4 bp 232.

(e) 4-Methoxy-2-(4-methoxy-2-methylthiophenyl)pyridine

A Grignard reagent was prepared from the product of step (d) above (12.3 g), magnesium (1.28 g) and iodine (1 crystal) in dry tetrahydrofuran (150 ml). 4-Methoxypyridine (5.76 g) was dissolved in dry tetrahydrofuran (300 ml) and stirred under nitrogen. The solution was cooled to −70° and treated with the above Grignard solution in one portion. After stirring for 10 minutes phenylchloroformate (6.6 ml) was added dropwise. After stirring at −70° for 30 minutes the mixture was allowed to warm up to room temperature. After stirring for 90 minutes the mixture was poured onto water and extracted with ether. The ether was washed with water and brine then dried and evaporated. The residue was taken up in toluene (250 ml) and stirred at room temperature. A solution of 3,4,5,6-tetrachloro-1,2-benzoquinone (13.0 g) in acetic acid (120 ml) was added dropwise. When addition was complete the mixture was stirred for a further 18 hours. The mixture was ice cooled and treated with a cold solution of sodium hydroxide (700 ml of 10%). After stirring for 10 minutes the mixture was filtered and separated. The aqueous filtrates were extracted with ether and the combined organic filtrates were extracted with dilute hydrochloric acid. The extracts were combined and basified with sodium hydroxide solution. The mixture was extracted with ether and the combined extracts washed with brine then dried and evaporated. Flash chromatography (1:1 ethyl acetate/petroleum ether) produced the subtitle compound as a clear oil 5.4 g. NMR (CDCl$_3$) d 8.50 (d,1H), 7.39 (d,1H), 7.60 (d,1H), 6.85 (d,1H), 6.77 (m,2H), 3.88 (s,3H), 3.86 (s,3H), 2.40 (s,3H).

The title compound was prepared using methods analogous to Example 25 (b), (c) and (d) via:

(f) 4-Methoxy-2-(4-methoxy-2-methylsulphinylphenyl)-pyridine MS M+ 277

(g) 2-[5-Methoxy-2-(4-methoxy-2-pyridinyl)phenylthio]-1H-benzimidazole MS M+ 363

(h) 2-[5-Methoxy-2-(4-methoxy-2-pyridinyl)phenylsulphinyl]-1H-benzimidazole mp 204°–207°

EXAMPLE 28

By methods analogous to those of Example 27 above, using the appropriate starting materials, were made the following compounds.

(a)
  (i) 2-[2-(4-Methoxy-2-pyridinyl)phenylthio]-4,5-dimethyl-1H-benzimidazol. MS M+ 361.
  (ii) 2-[2-(4-Methoxy-2-pyridinyl)phenylsulphinyl]-4,5-dimethyl-1H-benzimidazol, mp 113°–115°.

(b)
  (i) 2-[2-(4-Methoxy-2-pyridinyl)phenylthio]-5-nitro-1H-benzimidazol. MS M+ 378.
  (ii) 2-[2-(4-Methoxy-2-pyridinyl)phenylsulphinyl]-5-nitro-1H-benzimidazol, mp 174°.

(c)
  (i) 5-Chloro-2-[2-(4-methoxy-2-pyridinyl)phenylthio]-1H-benzimidazol. MS M+ 367/369.
  (ii) 5-Chloro-2-[2-(4-methoxy-2-pyridinyl)phenyl sulphinyl]-1H-benzimidazol, mp 127°–135°.

(d)
  (i) 5,6-Dimethoxy-2-[2-(4-methoxy-2-pyridinyl)phenyl thio]-1H-benzimidazol. MS M+ 393.
  (ii) 5,6-Dimethoxy-2-[2-(4-methoxy-2-pyridinyl)phenyl sulphinyl]-1H-benzimidazol, mp 150° (d).

(e)
  (i) Ethyl 6-ethoxy-2-[2-(4-methoxy-2-pyridinyl) phenylthio]-1H-benzimidazole-5-carboxylate, mp 76°–78°.
  (ii) Ethyl 6-ethoxy-2-[2-(4-methoxy-2-pyridinyl) phenylsulphinyl]-1H-benzimidazole-5-carboxylate, mp 108°–110°.

(f)
  (i) 4,7-Dimethoxy-2-[2-(4-methoxy-2-pyridinyl)phenyl thio]-1H-benzimidazol. MS M+ 393.
  (ii) 4,7-Dimethoxy-2-[2-(4-methoxy-2-pyridinyl)phenyl sulphinyl]-1H-benzimidazol, mp 217°–218°.

(g)
  (i) 2-[2-(4-Ethoxy-2-pyridinyl)phenylthio-1H-benzimidazole. MS M+ 347.
  (ii) 2-[2-(4-Ethoxy-2-pyridinyl)phenylsulphinyl-1H-benzimidazole, mp 131°.

(h)
  (i) 2-[2-(4-(1-Methylethoxy)-2-pyridinyl)phenylthio]-1H-benzimidazol. MS M+ 361.
  (ii) 2-[2-(4-(1-Methylethoxy)-2-pyridinyl)phenyl sulphinyl]-1H-benzimidazol, mp 122°–124°.

(j)
(i) 2-[2-(4-(4-Morpholinyl)-2-pyridinyl)phenylthio]-1H-benzimidazol. MS M+ 388.
(ii) 2[2-(4(4-Morpholinyl)-2-pyridinyl)phenyl sulphinyl]-1H-benzimidazol, mp 166°-⅛°.

via (iii) 1-[2-(2-Methylthio phenyl)-4-pyridinyl] morpholin. MS m/e 286 (M+) 271 (100%).

(k)
(i) 2-[2-(1H-Benzimidazol-2-yl thio)phenyl]-N,N-dimethyl-4-pyridinamine. MS M+ 346.
(ii) 2-[2-(1H-Benzimidazol-2-yl sulphinyl) phenyl]-N,N-dimethyl-4-pyridinamin, mp 190°-191° (d).

(l)
(i) 6-[2-(4-Methoxy-2-pyridinyl)phenylthio-2H,5H-dioxolo[4,5-f]benzimidazol, mp 210°-212°.
(ii) 6-[2-(4-Methoxy-2-pyridinyl)phenylsulphinyl-2H,5H-dioxolo[4,5-f]benzimidazol, mp 174°-6°.

(m)
(i) 2-[2-(4-Propyloxy-2-pyridinyl)phenylthio]-1H-benzimidazole. MS M+ 361.
(ii) 2-[2-(4-Propyloxy-2-pyridinyl)phenylsulphinyl]-1H-benzimidazol, mp 92°-4°.

(n)
(i) 2-[5-Chloro-2-(4-methoxy-2-pyridinyl)phenylthio]-1H-benzimidazol. MS(M+367/379.
(ii) 2-[5-Chloro-2-(4-methoxy-2-pyridinyl)phenyl sulphinyl]-1H-benzimidazol. MS(M+1) (FAB) 384.

via (iii) Methyl 4-chloro-2-(N,N-dimethylthiocarbamoyloxy) benzoat. MS M+ 273/275.
(iv) Methyl 4-chloro-2-(N,N-dimethylcarbamoylthio) benzoat. MS M+ 273/275.
(v) 4-Chloro-2-mercapto benzoic acid. MS M+ 188/190
(vi) 4-Chloro-2-methylthio benzoic acid. MS M+ 202/204
(vii) 4-Chloro-2-methylthio benzoyl chloride. MS M+ 220/222/224.
(viii) 2-[4-Chloro-2-methylthiophenyl]-1,4-dihydropyridin-4-one. M+251.
(ix) 4-Chloro-2-(4-chloro-2-methylthiophenyl)pyridine. MS M+ 269/271/273.
(x) 2-(4-Chloro-2-methylthiophenyl)-4-methoxy pyridin. MS M+ 265/267.
(xi) 2-(4-Chloro-2-methylsulphinylphenyl)-4-methoxypyridine. MS M+ 281/283.

(o)
(i) 2-[5-Methoxy-2-(4-methoxy-2-pyridinyl)phenyl thio]-1H-benzimidazol. MS M+ 347.
(ii) 2-[5-Methoxy-2-(4-methoxy-2-pyridinyl)phenyl sulphinyl]-1H-benzimidazol. MS FAB M++1 364.

via (iii) Methyl 4-methyl-2-(N,N-dimethylthiocarbamoyl oxy)benzoat. M+253.
(iv) Methyl 4-methyl-2-(N,N-dimethylcarbamoylthio) benzoat. M+253.
(v) 2-Mercapto-4-methyl benzoic acid. M+168.
(vi) 4-Methyl-2-methylthio benzoic acid. M+182.
(vii) 4-Methyl-2-methylthio benzoyl chloride. M+200/202.
(viii) 1,4-Dihydro-2-(4-methyl-2-methylthiophenyl) pyridin-4-one. M+231.
(ix) 4-Chloro-2-(4-methyl-2-methylthiophenyl)pyridine. M+249/251.
(x) 4-Methoxy-2-(4-methyl-2-methylthiophenyl)pyridine M+245.
(xi) 4-Methoxy-2-(4-methyl-2-methylsulphinylphenyl) pyridin. M+261.

(p)
(i) Methyl 2-(2-(4-methoxy-2-pyridinyl)phenylthio-6-methyl-1H-benzimidazole-5-carboxylate, mp 108°-110°.
(ii) Methyl 2-(2-(4-methoxy-2-pyridinyl)phenyl sulphinyl-6-methyl-1H-benzimidazole-5-carboxylate, mp 138°-140°.

via (iii) Methyl 6-methyl-2-methylthio-1H-benzimidazole-5-carboxylate. MS MW + bp 236.
(iv) Methyl 6-methyl-2-methylsulphinyl 1H-benzimidazole-5-carboxylate. MS MW 268 bp 237
(v) 5-Methoxy-1-(2-methylthiophenyl)-pent-4-ene-1,3-dione.
(vi) 1,4-Dihydro-2-(2-methylthiophenyl)pyridin-4-one. MS m/e 218 (M+1) 202 (100%).
(vii) 4-Chloro-2-(2-methylthiophenyl)pyridine. MS m/e 235/237 220 (100%).
(viii) 4-Methoxy-2-(2-methylthiophenyl)pyridine. MS m/e 231 (M+) 216 (100%).
(ix) 4-Methoxy-2-(2-methylsulphinylphenyl)pyridine. MS (FAB) M+1 248 (EI) bp 232.

EXAMPLE 29

5,6-Dimethoxy-2-[5-methoxy-2-(2-pyridinyl)phenyl sulphinyl]-1H-benzimidazole (a)

5,6-Dimethoxy-2-(5-methoxy-2-nitrophenylthio)-1H-benzimidazole 5,6-Dimethoxy benzimidazole-2-thione (4.0 g), 2-chloro-4-methoxy nitrobenzene (3.6 g) and potassium carbonate (2.65 g) were stirred together in dry dimethyl formamide (30 ml) at 95° for 3 days. The cooled mixture was poured onto water (300 ml) and the precipitate collected. The solid was washed with water and dried to leave the sub-title compound as a pale yellow solid, MS 361 bp 207.

(b)

2-[-5,6-Dimethoxy-2-1H-benzimidazolylthio]-4-methoxy benzenamine

The product of step (a) above (6.3 g), iron powder (6.3 g) and ammonium chloride (6.3 g) were stirred together with ethanol (63 ml) and water (120 ml) and heated under reflux for 1 hour. The hot mixture was filtered and the residue washed with hot ethyl acetate (500 ml). The combined filtrates were separated and the aqueous phase extracted with ethyl acetate. The combined ethyl acetate extracts were washed with water and brine, then dried and evaporated to leave a foam. Upon trituration with ether the sub-title compound was formed as a grey solid, MS MW bp 331.

(c)

5,6-Dimethoxy-2-[5-methoxy-2-(2-pyridinyl)phenylthio]-1H-benzimidazole

The product of step (b) above (500 mg) was treated with concentrated hydrochloric acid (0.8 ml) and water (0.8 ml) to form a paste. The paste was stirred at 0°-10° and a solution of sodium nitrite (105 mg) in water (0.5 ml) added dropwise. After stirring for 40 minutes the resultant solution was added slowly to pyridine (5 ml) stirred at 80°. The mixture was stirred for a further 40 minutes then concentrated in vacuo. The residue was slurried with 0.880 ammonia and the mixture again concentrated in vacuo. The residue was slurried with water and extracted with ethyl acetate. The ethyl acetate was washed with water and brine, then dried and evaporated to leave a brown gum. Flash chromatography produced the required product as a pale brown solid, MS MW 393 bp 216.

(d) 5,6-Dimethoxy-2-[5-methoxy-2-(2-pyridinyl)phenyl sulphinyl]-1H-benzimidazole The product of step (c) above (370 mg) was dissolved in ethyl acetate (90 ml) and cooled to −10°. To the stirred solution was added a solution of m-chloroperbenzoic acid (191 mg of 85%) in ethyl acetate (10 ml). After stirring for 1 hour the solution was washed with sodium bicarbonate solution, sodium metabisulphite solution, water and brine then dried and evaporated. The residue was flash chromatographed to afford the title compound as a buff solid, mp 208°–210°.

EXAMPLE 30

By methods analogous to those of Example 29, using the appropriate starting materials, the following compounds were made:
(a)
  (i) 2-[2-(4-Methyl-2-pyridinyl)phenylthio]-1H-benzimidazole, MS m/z 317 bp 200.
  (ii) 2-[2-(4-Methyl-2-pyridinyl)phenylsulphinyl]-1H-benzimidazole, mp 203°–4°.
(b)
  (i) 2-[2-(2-Pyridinyl-5-(1-pyrrolidinyl)phenylthio]-1H-benzimidazole, mp 240° (d).
  (ii) 2-[2-(2-Pyridinyl-5-(1-pyrrolidinyl)phenyl sulphinyl]-1H-benzimidazole. mp 90° (d).
(c)
  (i) 5-Methoxy-2-[2-(4-methyl-2-pyridinyl)phenylthio]-1H-benzimidazole, mp 81°.
  (ii) 5-Methoxy-2-[2-(4-methyl-2-pyridinyl)phenyl sulphinyl]-1H-benzimidazole, mp 111°.
(d)
  (i) Methyl 2-[2-(4-methyl-2-pyridinyl)phenylthio]-1H-benzimidazole-5-carboxylate, MS M+ 372.
  (ii) Methyl 2-[2-(4-methyl-2-pyridinyl)phenyl sulphinyl]-1H-benzimidazole -5-carboxylate, mp 70°.
(e)
  (i) 2-[2-(2-Pyridinyl)phenylthio]-1H-imidazole, MS m/e 253 (M+) 186 (100%).
  (ii) 2-[2-(2-Pyridinyl)phenylsulphinyl]-1H-imidazole, MS m/e 270 (M+1=100%) (FAB).

EXAMPLE 31

2-[2-(1H-Benzimidazol-2-yl sulphinyl)phenyl]-1-methyl-1H-benzimidazole (a) 2-(2-Methylthiophenyl)-1H-benzimidazole 2-Methylthio benzoic acid chloride (4 g), o-phenylenediamine (2.32 g) and polyphosphoric acid (64 g) were heated at 135° with stirring for 24 hours. The reaction mixture was poured onto ice, basified with sodium hydroxide solution and extracted with ethyl acetate which was washed with brine, dried over magnesium sulphate and evaporated to dryness to leave the sub-title compound as pale yellow solid, MS MW 240 bp 225.

(b) 1-Methyl-2-(2-methylthiophenyl)-1H-benzimidazole

The product of step (a) above (3.25 g), methyl iodide (1.92 g) and potassium carbonate (5.2 g) were stirred together in dry dimethylformamide (50 ml) at room temperature for 24 hours. The reaction mixture was poured into brine and extracted into ethyl acetate, the extract was washed with excess brine, dried over magnesium sulphate and evaporated to dryness in vacuo and the residue was purified by flash chromatography (SiO2/CH2Cl2 9:1 ethyl acetate) to afford the sub-title compound as yellow solid, MS MW 254 bp 239.

(c) 1-Methyl-2-(2-methylsulphinylphenyl)-1H-benzimidazole

The product of step (b) above (2 g) was dissolved in dichloromethane (50 mls) and cooled to −10° with stirring. 85% m-chloroperbenzoic acid (1.6 g) was added portionwise. The reaction mixture was slowly warmed to room temperature and after 3 hours the reaction was complete. The reaction mixture was washed with aqueous metabisulphite solution, then bicarbonate solution and finally brine, dried over magnesium sulphate and evaporated to dryness in vacuo, then the residue was purified by flash chromatography (SiO2/ethyl acetate 3:2 CH2Cl2) to afford the sub-title compound as a yellow crystalline solid, mp 157°–159°.

(d) 2-[2-(1H-Benzimidazol-2-yl thio)phenyl]-1-methyl-1H-benzimidazole

The product of step (c) above (1.83 g) was heated at reflux temperature with trifluoroacetic anhydride (10 ml) and dry dichloromethane (15 ml) for 30 minutes. The whole was evaporated to dryness and the resulting oil was dissolved in dry methanol (20 mls) and triethylamine (20 ml). 2-(Phenylsulphonyl)-1H-benzimidazole (1.75 g) was added to the solution and the whole was heated at 70° for 15 minutes before evaporation to dryness.

The pale yellow residue was dissolved in iso-propanol (50 ml) and heated at reflux temperature for 30 minutes before the addition of sodium borohydride (0.26 g) and further heating for 1 hour at reflux temperature and 18 hours at 50°.

The volume of iso-propanol was reduced to approximately 5 ml and the reaction mixture was poured into brine, extracted with dichloromethane, dried over magnesium sulphate and evaporated to dryness in vacuo. The residue was purified by flash chromatography (SiO2/ethyl acetate 1:9 CH2Cl2) to afford the sub-title compound as a white powder, mp 246°–247°.

(e) 2-[2-(1H-benzimidazol-2-yl sulphinyl)phenyl]-1-methyl-1H-benzimidazole

The product of step (d) above (0.99 g) was dissolved in dichloromethane (60 ml) and methanol (5 ml) and cooled to −10°. 85% m-Chloroperbenzoic acid (0.56 g) was added and the whole was slowly warmed to room temperature with stirring. After 2 hours the reaction mixture was washed with metabisulphate solution, then bicarbonate solution and finally with brine, dried over magnesium sulphate and evaporated to dryness in vacuo and the residue was purified by flash chromatography (SiO2/CH2Cl2 2:3 ethyl acetate) to afford the title compound as a white solid, mp 164°.

EXAMPLE 32

By methods analogous to those of Example 31 were made the following compounds:
(a)
  (i) 2-[2-(1H-2-Benzimidazolylthio)phenyl]-6-chloro-1-methyl-1H-benzimidazole, mp 228°–230°.

(ii) 2-[2-(1H-2-Benzimidazolylsulphinyl)phenyl]-6-chloro-1-methyl-1H-benzimidazole, mp 179°–182°.

via (iii) 5-Chloro-2-(2-methylthio phenyl)-1H-benzimidazole, mp 221°–222°.

(iv) 6-Chloro-1-methyl-2-(2-methylthio phenyl)-1H-benzimidazole. MS M+ 288/290 bp 273/275.

(v) 6-Chloro-1-methyl-2-(2-methylsulphinyl phenyl)-1H-benzimidazole, mp 124°–126°.

(b)

(i) 2-[2-(1H-2-Benzimidazolylthio)phenyl]-5-chloro-1-methyl-1H-benzimidazole, mp 124°–125°.

(ii) 2-[2-(1H-2-Benzimidazolylsulphinyl)phenyl]-5-chloro-1-methyl-1H-benzimidazole, mp 217°–220°.

via (iii) 5-Chloro-1-methyl-2-(2-methylthio phenyl)-1H-benzimidazole. MS M+ 304/306 bp 289/291.

(iv) 5-Chloro-1-methyl-2-(2-methylsulphinyl phenyl)-1H-benzimidazol. MS M+ 288/290 bp 273/275.

(c)

(i) 2-[2-(1H-2-Benzimidazolylthio)phenyl]-5,6-dichloro-1-methyl-1H-benzimidazole, mp 226°–227°.

(ii) 2-[2-(1H-2-Benzimidazolylsulphinyl)phenyl]-5,6-dichloro-1-methyl-1H-benzimidazole, mp 183°–185°.

via (iii) 5,6-Dichloro-2-(2-methylthio phenyl)-1H-benzimidazole. MS M+ 308/310/312 bp 293.

(iv) 5,6-Dichloro-1-methyl-2-(2-methylthio phenyl)-1H-benzimidazole. MS (FAB) M+1 323/325/327 bp 323.

(v) 5,6-Dichloro-1-methyl-2-(2-methylsulphinyl phenyl)-1H-benzimidazole. MS M+ 338/340/342 bp 156/158.

(d)

(i) 2-[2-(5-Methoxy-1H-2-benzimidazolylthio)phenyl]-1-methyl-1H-benzimidazol, mp 90° (d).

(ii) 2-[2-(5-Methoxy-1H-2-benzimidazolylsulphinyl)phenyl]-1-methyl-1H-benzimidazole, mp 162°–165° (d).

(e)

(i) Methyl 2-[2-(1-methyl-1H-2-benzimidazolyl)phenylthio]-1H-benzimidazole-5-carboxylate. MS M+ 414.

(ii) Methyl 2-[2-(1-methyl-1H-2-benzimidazolyl)phenylsulphinyl]-1H-benzimidazole-5-carboxylate, mp 190°.

EXAMPLE 33

2-[2-(6,7-Dimethoxy-1-isoquinolinyl)phenylsulphinyl]-1H-benzimidazole (a) N-[(3,4-Dimethoxyphenyl)ethyl]-2-methylthio benzamide 2-(3,4-Dimethoxyphenyl)ethylamine (4.8 ml), poly(4-vinylpyridine) (PVP) (5.7 g) and 2-methylthiobenzoyl chloride (5.3 g) were stirred in dichloromethane (50 ml) with cooling in a water bath at 20° for one night. The PVP was filtered off and washed with CHCl₃. Evaporation of the extracts followed by flash chromatography (ethyl acetate/petroleum ether) gave the sub-title compound, mp 94°–95°.

(b) 6,7-Dimethoxy-1-[(2-methylthio)phenyl]-3,4-dihydroisoquinoline

The product of step (a) above was heated with phosphorous pentoxide (6 g) in dry acetonitrile (500 ml) under reflux with stirring for 2 hours. The mixture was cooled, carefully treated with water and neutralised with solid NaHCO₃ and extracted with ethyl acetate producing, on evaporation, the sub-title compound as an oil, MS Electron Impact (EI) 298 (100%, M-15).

(c) 6,7-Dimethoxy-[(2-methylthio)phenyl]isoquinoline

The product of step (b) above (3.4 g) was treated with sulphur (2 g) under reflux in xylene (80 ml) while additional quantities of sulphur (0.2 g) were added every 3 days, for 2 weeks. The solvent was evaporated off and the residue was chromatographed (ethyl acetate/petroleum ether) producing the sub-title compound as an oil, MS 311 (M,5%), 296 (M-15, 100%).

(d) 6,7-Dimethoxy-1-[(2-methylsulphinyl)phenyl]isoquinoline

The product of step (c) above was treated with 85% m-Chloroperbenzoic acid (1.58 g) in ethyl acetate to produce, after chromatography, the sub-title compound, mp 64°.

(e) Bis[2-(6,7-dimethoxy-1-isoquinolinyl)phenyl disulphide]

The product of step (d) above (1.14 g) and trifluoroacetic anhydride (0.98 ml) were treated in CH₂Cl₂ (20 ml) solution under reflux for 1 hour. The solvent was evaporated off and the resulting gum was heated in triethylamine (5 ml) and methanol (25 ml) under reflux for 1 hour. The solvents were removed and the residue chromatographed (ethyl acetate/petroleum ether) yielding the sub-title compound as a white solid, MS 593 (M+1, 5%), 296 (100%).

(f) 2-[2-(6,7-Dimethoxy-1-isoquinolinyl)phenylthio]-1H-benzimidazole

The product of step (e) above (59 mg) was heated with sodium cyanoborohydride (6 mg) in the presence of 2-chlorobenzimidazole (31 mg) in acetic acid (1 ml) and iso-propanol (5 ml) for 1 hour under nitrogen at 80°. The product was neutralised with NaHCO₃ aqueous and extracted with ethyl acetate giving the sub-title compound as a solid, MS 413 (M,70%), 296 (100%).

(g) 2-[2-(6,7-Dimethoxy-1-isoquinolinyl)phenylsulphinyl]-1H-benzimidazole

The product of step (f) above was dissolved in 1:1 CH₂Cl₂-CHCl₃ (10 ml), treated with 85%m-Chloroperbenzoic acid (24 mg) at −5°, and worked up in aqueous NaHCO₃ to give the title compound. NMR (CDCl₃)d, 8.5 (d,1H), 8.35 (dd,1H), 7.26 (1H,s), 7.21 (1H,s), 7.7–7.2 (complex,8H), 4.30 (s,3H), 3.85 (s,3H)ppm, mp 250° (d).

EXAMPLE 34

2-[2-(4-Methoxy-2-pyridinyl)-3-thienylsulphinyl]-1H-benzimidazole (a) 4-Methoxy-1-phenoxycarbonyl-2-(2-thienyl)-1,2-dihydro pyridine 2-Iodothiophene (21 g) was reacted with magnesium (2.43 g) in dry diethyl ether (200 ml) and a crystal of iodine under reflux in a nitrogen atmosphere, for 1 hour. The solution was decanted into a solution of 4-methoxy pyridine (7.94 g) in dry tetrahydrofuran (200 ml) at −25° with vigorous stirring. After 5 minutes, phenyl chloroformate (9.17 ml) was added dropwise, and the mixture allowed to warm to room temperature overnight. Aqueous work-up and ethyl acetate extraction gave the sub-title compound as a brown oil, MS (EI) 313 (M,20%), 230 (70%), 220 (100%).

(b) 4-Methoxy-2-(2-thienyl)pyridine

The product of step (a) above (24 g) was dissolved in toluene (240 ml) at room temperature and treated with tetrachloro-1,2-benzoquinone (18.9 g) in a solution of acetic acid (90 ml) dropwise during 0.5 hour and stirred overnight. Ice was added and the mixture was basified with 40% aqueous NaOH producing a black precipitate. The mixture was filtered, washed with toluene, then $CH_2Cl_2$. The combined filtrates were cooled and extracted with concentrated HCl acid (6 times 100 ml). Neutralisation of the aqueous solution with $NaHCO_3$ (solid) and ethyl acetate extraction, and chromatography gave the sub-title compound, mp 43°–45°.

(c) 4-Methoxy-2-(3-methylthio-2-thienyl)pyridine

The product of step (b) above (5 g) dissolved in dry diethyl ether (100 ml) was cooled to −50° and treated with butyl lithium in hexane (2.2M, 13 ml) dropwise during 0.5 hour. The mixture was warmed to −10° for 10 minutes, then cooled to −30°. Dimethyl disulphide (3.5 ml) was then added dropwise. The mixture was maintained at −30° for 0.5 hour then warmed up to room temperature during several hours. Aqueous work-up and ethyl acetate extraction gave the sub-title compound as an oil.

(d) 4-Methoxy-2-(3-methylsulphinyl-2-thienyl)pyridine

The product of step (c) above was dissolved in ethyl acetate (100 ml) and cooled to −10°. m-Chloroperbenzoic acid (2.98 g) was added and after 1.5 hour the mixture was worked-up then chromatographed (ethyl acetate) to give the sub-title compound as a solid, mp 103°–105°.

(e) [2-(4-Methoxy-2-pyridinyl)-3-thienyl]disulphide

The product of step (d) above (1.61 g) and trifluoroacetic anhydride (1.79 ml) were heated under reflux in dichloromethane (50 ml) producing a copious white precipitate during 1.5 hour. The solvent was evaporated off and the residue was heated under reflux with methanol (10 ml) and triethylamine (10 ml) for 0.5 hour. Evaporation to dryness in vacuo, aqueous work-up, extraction in ethyl acetate and chromatography gave the sub-title compound as a gum. MS (FAB) 445 (M+1), (5%), 222 (100%).

(f) 2-[2-(4-Methoxy-2-pyridinyl)-3-thienylthio]-1H-benzimidazole

The product of step (e) above was reacted with sodium cyanoborohydride (0.236 g) and 2-chlorobenzimidazole (1.14 g) in iso-propanol (20 ml) and acetic acid (5 ml) at 80° for 1 hour. Cooling, $NaHCO_3$ work-up, ethyl acetate extraction and washing with diethyl ether gave the sub-title compound as a white solid, MS (EI) 339 (M,100%), 306 (80%).

(g) 2-[2-(4-Methoxy-2-pyridinyl)-3-thienylsulphinyl]-1H-benzimidazole The product of step (f) above (1.25 g) was dissolved in chloroform (500 ml). The stirred solution was cooled to −5° and m-Chloroperbenzoic acid (85%, 0.75 g) was added in portions during 10 minutes. After 1 hour, $NaHCO_3$ work-up and chromatography gave the title compound, mp 192°.

EXAMPLE 35

By methods analogous to those of Example 34 were made the following compounds:

(i) 5-Methyl-2-[3-(2-pyridinyl-thien-2yl thio]-1H-benzimidazole, MS m/e 323 (70%, M+) bp 290.

(ii) 5-Methyl-2-[3-(2-pyridinyl-thien-2-yl sulphinyl]-1H-benzimidazole, mp 100° (d).

EXAMPLE 36

2-[2-(4-Methoxy-2-pyridinyl)-phenylsulphinyl]-1H-benzimidazole-5-amine

The compound of Example 28 (b) (ii) was hydrogenated over a 10% Palladium-carbon catalyst at 3 atmospheres pressure in ethanol. The catalyst was filtered off and the ethanol was evaporated to leave the title compound, mp 192°–193°.

EXAMPLE 37

1-[2-[2-(1H-2-Benzimidazolylsulphinyl)phenyl 4-pyridinyloxy]propan-2-ol, (FAB ms M+ +1)

The title compound was derived from the compound of Example 25 m) above using a $NaBH_4$/ethanol standard reduction.

EXAMPLE 38

2-(2-1H-Benzimidazol-2-yl sulphinyl)-phenyl-imidazo[1,2-a]pyridine (a) 2-(2Bromophenyl)imidazo[1,2-a]pyridine A solution of 2-aminopyridine (1.63 g) and 2-bromo-1-(2-bromophenyl)-ethanone (4.8 g) in dry ethanol (40 mls) was heated under reflux for 1 hour. The mixture was concentrated in vacuo. The residue was treated with dilute sodium bicarbonate solution and extracted with ethyl acetate. The ethyl acetate was washed with water and brine then dried and evaporated. Flash chromatography produced the sub-title compound as a light grey oil. MS MW 272/274 bp 272.

(b) 2-(2-Methylthiophenyl)imidazo[1,2-a]pyridine

The product of step (a) above (546 mg) was dissolved in dry ether (10 ml) and stirred under a nitrogen atmosphere at −60°. A solution of n-butyl lithium (1.25 ml of 1.6 M) was added dropwise. After stirring for 5 minutes methyl disulphide (179 ml) was added dropwise and the mixture stirred for a further 45 minutes. The mixture was allowed to warm up to room temperature then quenched with water. The layers were separated and the aqueous layer extracted with ethyl acetate. The combined organic solution was washed with water and brine then dried and evaporated to leave the sub-title compound as a gum. MS MW 240 bp 207.

(c) 2-(2-Methylsulphinyl)imidazo[1,2-a]pyridine

The sub-title compound was prepared from the product of step (b) above using a method analogous to that of Example 31 (c) above. MS MW 257 bp 78.

(d) 2-(2-1H-Benzimidazol-2-yl thio)phenyl-imidazo [1,2-a]pyridine

The sub-title compound was prepared from the product of step (c) above using a method analogous to that of Example 31 (d) above. MS MW 342 bp 225.

(e) 2-(2-1H-Benzimidazol-2-yl sulphinyl)phenyl-imidazo [1,2-a]pyridine

The title compound was prepared from the product of step (d) above using a method analogous to that of Example 31 (e) above. MS (FAB) M+1/bp 359.

EXAMPLE 39

| | |
|---|---|
| (a) Pellet Formulation | |
| A pellet (220 mg) containing: | |
| a compound of formula I | 50 mg |
| lactose | 103 mg |
| starch | 50 mg |
| magnesium stearate | 2 mg |
| hydroxypropylcellulose | 15 mg |
| (b) Capsule Formulation | |
| A gelatin-shell hard capsule containing 350 mg of the core portion consisting of: | |
| a compound of formula I | 40 mg |
| lactose | 200 mg |
| starch | 70 mg |
| polyvinylpyrrolidone | 5 mg |
| crystalline cellulose | 35 mg |
| (c) Granule Formulation | |
| One gram of granules containing: | |
| a compound of formula I | 200 mg |
| lactose | 450 mg |
| corn starch | 300 mg |
| hydroxypropylcellulose | 50 mg |

What is claimed is:
1. A compound of formula I,

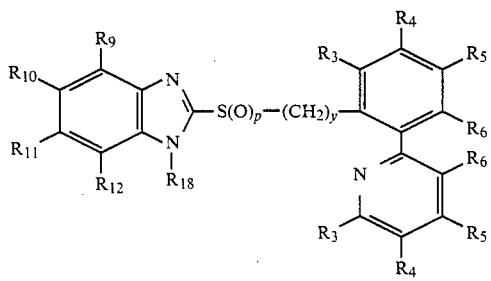

in which $R_3$ to $R_6$ and $R_9$ to $R_{12}$, which may be the same or different, are each hydrogen, halogen, phenoxy, alkyl $C_1$ to $C_6$, fluoroalkyl $C_1$ to $C_6$, alkanoyl $C_1$ to $C_6$, benzoyl, $RS(O)_n-$, $NO_2$, $NR_{16}R_{17}$, NHCOR, —COOH or an ester derived from a $C_1$ to $C_6$ alcohol or an unsubstituted or a mono- or dialkyl $C_1$ to $C_6$ substituted amide thereof, or alkoxy $C_1$ to $C_6$ optionally substituted by phenyl, y is 0 or 1,
p is 0 or 1,
n is 0, 1, or 2,
$R_{18}$ is hydrogen, COR, COOR, or alkyl $C_1$ to $C_6$, said alkyl being optionally substituted by —OCOR or by phenyl,
R, $R_{16}$, and $R_{17}$, which may be the same or different, are each hydrogen, phenyl or alkyl $C_1$ to $C_6$ optionally substituted by phenyl, the phenyl groups in turn optionally being substituted by alkyl $C_1$ to $C_6$,
or a pharmaceutically acceptable salt thereof.

2. A compound according to claim 1 which p is 1.
3. A compound in accordance with claim 1 wherein y is 0.
4. A compound in accordance with claim 1 wherein $R_3$ to $R_6$ are selected from hydrogen, halogen, and alkoxy $C_1$ to $C_6$.
5. A compound in accordance with claim 1 wherein $R_9$ to $R_{12}$ are selected from hydrogen, alkyl $C_1$ to $C_6$ and alkoxy $C_1$ to $C_6$.
6. A compound in accordance with claim 1 selected from
2-[4-Dimethylamino-2-(4-methoxy-2-pyridinyl)phenyl thio]-1H-benzimidazole,
2-[4-Dimethylamino-2-(4-methoxy-2-pyridinyl)phenyl sulphinyl]-1H-benzimidazole,
2-[5-Methoxy-2-(4-methoxy-2-pyridinyl)phenylthio]-1H-benzimidazole,
2-[5-Methoxy-2-(4-methoxy-2-pyridinyl)phenylsulphinyl]-1H-benzimidazole,
2-[2-(4-Methoxy-2-pyridyl)-phenyl thio]-1H-benzimidazole,
2-[2-(4-Methoxy-2-pyridyl)-phenyl sulphinyl]-1H-benzimidazole,
or a pharmaceutically acceptable salt thereof.

7. A compound in accordance with claim 1 selected from
2-[2-(2-Pyridyl)-phenylthio]-1H-benzimidazole,
2-[2-(2-Pyridyl)-phenylsulphinyl]-1H-benzimidazole,
5-Chloro-2-(2-(2-pyridyl)-phenylthio)-1H-benzimidazole,
5-Chloro-2-(2-(2-pyridyl)-phenylsulphinyl)-1H-benzimidazole,
Methyl 2-(2-(2-pyridyl)-phenylthio)-1H-benzimidazole-5-carboxylate,
Methyl 2-(2-(2-pyridyl)-phenylsulphinyl)-1H-benzimidazole-5-carboxylate,
4-Trifluoromethyl-2-[2-(2-pyridyl)-phenylthio]-1H-benzimidazole,
4-Trifluoromethyl-2-[2-(2-pyridyl)-phenylsuphinyl]-1H-benzimidazole,
2-[5-Chloro-2-(2-pyridyl)-phenylthio]-5-methoxy-1H-benzimidazole,
2-[5-Chloro-2-(2-pyridyl)-phenylsulphinyl]-5-methoxy-1H-benzimidazole,
5,6-Dimethyl-2-[2-(2-pyridyl)-phenylthio]-1H-benzimidazole,
5,6-Dimethyl-2-[2-(2-pyridyl)-phenylsulphinyl]-1H-benzimidazole,
5-Methyl-2-[2-(2-pyridyl)-phenylthio]-1H-benzimidazole,
5-Methyl-2-[2-(2-pyridyl)-phenylsulphinyl]-1H-benzimidazole,
5-(4-Methylphenylsulphonyl)-2-[2-(2-pyridyl)-phenyl thio]-1H-benzimidazole, 5-(4-Methylphenylsulphonyl)-2-[2-(2-pyridyl)-phenyl sulphinyl]-1H-benzimidazole,
N-[4-(4,7-Dimethoxy-1H-benzimidazol-2-yl thio)-3-(2-pyridyl)-phenyl]acetamide,
N-[4-(4,7-Dimethoxy-1H-benzimidazol-2-yl sulphinyl)-3-(2-pyridyl)-phenyl]acetamide,
2-[2-(2-Pyridyl)-phenyl methylthio]-1H-benzimidazole,
2-[2-(2-Pyridyl)-phenyl methylsulphinyl]-1H-benzimidazole,
1-Methyl-2-[2-(2-pyridyl)-phenylsulphinyl]-1H-benzimidazole,
5,6-Diethoxy-2-[2-(2-pyridyl)-phenylthio]-1H-benzimidazole,
5,6-Diethoxy-2-[2-(2-pyridyl)-phenylsulphinyl]-1H-benzimidazole,
Phenylmethyl 2-[2-(2-pyridyl)-phenylthio] benzimidazole-1-carboxylate,
Phenyl [2-[2-(2-pyridyl)phenylthio]-1H-benzimidazol-5-yl]methanone,
Phenyl [2-[2-(2-pyridyl)phenylsulphinyl]-1H-benzimidazol-5-yl] methanone,
Phenylmethyl 2-[2-(2-pyridyl)-phenylsulphinyl] benzimidazole-1-carboxylate,
5-Methoxy-2-[2-(4-methoxy-2-pyridyl)phenylthio]-1H-benzimidazole,
5-Methoxy-2-[2-(4-methoxy-2-pyridyl)phenylsulphinyl]-1H-benzimidazole,
2-[2-(4-Ethyl-2-pyridinyl)phenylthio]-1H-benzimidazole,
2-[2-(4-Ethyl-2-pyridinyl)phenylsulphinyl]-1H-benzimidazole,
Methyl 2-[2-(4-methoxy-2-pyridinyl)phenylthio]-1H-benzimidazole-5-carboxylate,
Methyl 2-[2-(4-methoxy-2-pyridinyl)phenyl sulphinyl]-1H-benzimidazole-5-carboxylate,
5-Methyl-2-[2-(4-methoxy-2-pyridinyl)phenylthio]-1H-benzimidazole,
5-Methyl-2-[2-(4-methoxy-2-pyridinyl)phenyl sulphinyl]-1H-benzimidazole,
2-[5-Methoxy-2-(4-methyl-2-pyridinyl)phenylthio]-1H-benzimidazole,
2-[5-Methoxy-2-(4-methyl-2-pyridinyl)phenyl sulphinyl]-1H-benzimidazole,
5-Methoxy-2-[2-(4-methoxy-2-pyridinyl)-5-methoxy phenylthio]-1H-benzimidazole,
5-Methoxy-2-[2-(4-methoxy-2-pyridinyl)-5-methoxy phenylsulphinyl]-1H-benzimidazole,
2-[2-(1H-2-Benzimidazolylthio)phenyl]-N-methyl-N-phenyl-4-pyridinamine,
2-[2-(1H-2-Benzimidazolylsulphinyl)phenyl]-N-methyl-N-phenyl-4-pyridinamine,
2-[5-Methoxy-2-(2-pyridinyl)phenylthio]-1H-benzimidazole,
2-[5-Methoxy-2-(2-pyridinyl)phenylsulphinyl-1H-benzimidazole,
5-Nitro-2-[4-nitro-2-(2-pyridyl)phenylthio]-1H-benzimidazole,
5-Nitro-2-[4-nitro-2-(2-pyridyl)phenylsulphinyl]-1H-benzimidazole,
4-Methoxy-2-[2-(4-methoxy-2-pyridinyl)phenylthio]-1H-benzimidazole,
4-Methoxy-2-[2-(4-methoxy-2-pyridinyl)phenyl sulphinyl]-1H-benzimidazole,
2-[2-(5-Methyl-2-pyridinyl)phenylthio]-1H-benzimidazole,
2-[2-(5-Methyl-2-pyridinyl)phenylsulphinyl-1H-benzimidazole,
2-[2-(4-Methoxy-6-methyl-2Pyridinyl)phenylthio]-1H-benzimidazole,
2-[2-(4-Methoxy-6-methyl-2-pyridinyl)phenyl sulphinyl]-1H-benzimidazole,
2-[2-(3-Methyl-2-pyridinyl)phenylthio]-1H-benzimidazole,
2-[2-(3-Methyl-2-pyridinyl)phenylsulphinyl]-1H-benzimidazole,
2-[2-(4-Methoxy-2-pyridinyl)phenylthio]-4,5-dimethyl-1H-benzimidazole,
2-[2-(4-Methoxy-2-pyridinyl)phenylsulphinyl]-4,5-dimethyl-1H-benzimidazole,
2-[2-(4-Methoxy-2-pyridinyl)phenylthio]-5-nitro-1H-benzimidazole,
2-[2-(4-Methoxy-2-pyridinyl)phenylsulphinyl]-5-nitro-1H-benzimidazole,
5-Chloro-2-[2-(4-methoxy-2-pyridinyl)phenylthio]-1H-benzimidazole,
5-Chloro-2-[2-(4-methoxy-2-pyridinyl)phenyl sulphinyl]-1H-benzimidazole,
5,6-Dimethoxy-2-[2-(4-methoxy-2-pyridinyl)phenyl thio]-1H-benzimidazole,
5,6-Dimethoxy-2-[2-(4-methoxy-2-pyridinyl)phenyl sulphinyl]-1H-benzimidazole,
Ethyl 6-ethoxy-2-[2-(4-methoxy-2-pyridinyl) phenylthio]-1H-benzimidazole-5-carboxylate,
Ethyl 6-ethoxy-2-[2-(4-methoxy-2-pyridinyl) phenylsulphinyl]-1H-benzimidazole-5-carboxylate,
4,7-Dimethoxy-2-[2-(4-methoxy-2-pyridinyl) phenyl thio]-1H-benzimidazole,
4,7-Dimethoxy-2-[2-(4-methoxy-2-pyridinyl) phenyl sulphinyl]-1H-benzimidazole,
2-[2-(4-Ethoxy-2-pyridinyl)phenylthio-1H-benzimidazole,
2-[2-(4-Ethoxy-2-pyridinyl)phenylsulphinyl-1H-benzimidazole,
2-[2-(4-(1-Methylethoxy)-2-pyridinyl)phenylthio]-1H-benzimidazole,
2-[2-(4-(1-Methylethoxy)-2-pyridinyl)phenyl sulphinyl]-1H-benzimidazole,
2-[2-(1H-Benzimidazol-2-yl thio)phenyl]-N,N-dimethyl-4-pyridinamine,
2-[2-(1H-Benzimidazol-2yl sulphinyl)phenyl]-N,N-dimethyl-4-pyridinamine,
2-[2-(4-Propyloxy-2-pyridinyl)phenylthio]-1H-benzimidazole,
2-[2-(4-Propyloxy-2-pyridinyl)phenylsulphinyl]-1H-benzimidazole,
2-[5-Chloro-2-(4-methoxy-2-pyridinyl)phenylthio]-1H-benzimidazole,
2-[5-Chloro-2-(4-methoxy-2-pyridinyl)phenyl sulphinyl]-1H-benzimidazole,
2-[5-Methoxy-2-(4-methoxy-2-pyridinyl)phenylthio]-1H-benzimidazole,
2-[5-Methoxy-2-(4-methoxy-2-pyridinyl)phenyl sulphinyl]-1H-benzimidazole,
Methyl 2-2-(4-methoxy-2-pyridinyl)phenylthio-6-methyl-1H-benzimidazole-5-carboxylate,
Methyl 2-2-(4-methoxy-2-pyridinyl)phenyl sulphinyl-6-methyl-1H-benzimidazole-5-carboxylate,
5,6-Dimethoxy-2-[5-methoxy-2-(2-pyridinyl) phenylthio]-1H-benzimidazole,
5,6-Dimethoxy-2-[5-methoxy-2-(2-pyridinyl)phenyl sulphinyl]-1H-benzimidazole,
2-[2-(4-Methyl-2-pyridinyl)phenylthio]-1H-benzimidazole,
2-[2-(4-Methyl-2-pyridinyl)phenylsulphinyl]-1H-benzimidazole, 5-Methoxy-2-[2-(4-methyl-2-pyridinyl)phenylthio]-1H-benzimidazole, 5-Methoxy-2-[2-(4-methyl-2-pyridinyl)phenyl sulphinyl]-1H-benzimidazole, Methyl 2-[2-(4-methyl-2-pyridinyl)phenylthio]-1H-benzimidazole-5-carboxylate, Methyl 2-[2-(4-methyl-2-pyridinyl)phenyl sulphinyl]-1H-benzimidazole-5-carboxylate, 2-[2-(4-Methoxy-2-pyridinyl)-phenylsulphinyl]-1H-benzimidazole-5-amine, or a pharmaceutically acceptable salt thereof.

8. A pharmaceutical formulation for prophylaxis or treatment of inflammatory conditions or for prevention or inhibition of gastric acid secretion comprising an effective amount of a compound of formula I as defined in claim 1, or a pharmaceutically acceptable salt thereof, in admixture with a pharmaceutically acceptable adjuvant, diluent or carrier.

9. A method for the prophylaxis or treatment of inflammatory conditions, or for prevention or inhibition of gastric acid secretion, which comprises administration of a compound of formula I as defined in claim 1, or a pharmaceutically acceptable salt thereof to a patient suffering from such a condition.

* * * * *